United States Patent
Alam

(10) Patent No.: US 10,780,264 B2
(45) Date of Patent: Sep. 22, 2020

(54) SKULL IMPLANTED ELECTRODE ASSEMBLY FOR BRAIN STIMULATION

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventor: Imran Khurshid Alam, Riyadh (SA)

(73) Assignees: National Guard Health Affairs, Riyadh (SA); King Saud bin Abdulaziz University for Health Science, Riyadh (SA); King Abdullah International Medical Research Center, Riyadh (SA)

( * ) Notice: Subject to any disclaimer, the term of this patent is extended or adjusted under 35 U.S.C. 154(b) by 176 days.

(21) Appl. No.: 16/109,148

(22) Filed: Aug. 22, 2018

(65) Prior Publication Data

US 2018/0361142 A1    Dec. 20, 2018

Related U.S. Application Data

(62) Division of application No. 15/277,589, filed on Sep. 27, 2016, now abandoned.

(51) Int. Cl.
| | |
|---|---|
| *A61N 1/05* | (2006.01) |
| *A61N 1/36* | (2006.01) |
| *A61B 5/0478* | (2006.01) |
| *A61B 5/00* | (2006.01) |
| *A61N 1/375* | (2006.01) |

(Continued)

(52) U.S. Cl.
CPC .......... *A61N 1/0539* (2013.01); *A61B 5/0478* (2013.01); *A61B 5/6864* (2013.01);
(Continued)

(58) Field of Classification Search
CPC .. A61N 1/0526; A61N 1/0529; A61N 1/0531; A61N 1/0534; A61N 1/0539;
(Continued)

(56) References Cited

U.S. PATENT DOCUMENTS

| 6,454,774 B1 | 9/2002 | Fleckenstein |
| 6,529,774 B1 * | 3/2003 | Greene .............. A61B 5/04001 |
| | | 600/378 |

(Continued)

FOREIGN PATENT DOCUMENTS

| WO | 2015/164143 A1 | 10/2015 |
| WO | 2016/069058 A1 | 5/2016 |

OTHER PUBLICATIONS

Berman, M.R., "A Tale of Two Carries; Bipolar Disease and Electroconvulsive Therapy", Medpage Today, 5 pages total, (Mar. 1, 2013).

(Continued)

*Primary Examiner* — Eugene T Wu
(74) *Attorney, Agent, or Firm* — Oblon, McClelland, Maier & Neustadt, L.L.P.

(57) ABSTRACT

A skull-implantable electrode assembly for delivering pulses of electric current to a patient's brain, comprising a conductor housed in an insulated conduit and threaded through an electrically-conductive cannulated skull screw. Details of the exterior construction are discussed, as well as electrode arrangements and methods of treating a medical ailment of a patient.

18 Claims, 21 Drawing Sheets

(51) Int. Cl.
 *A61N 1/378* (2006.01)
 *A61B 5/04* (2006.01)

(52) U.S. Cl.
 CPC ....... *A61N 1/3606* (2013.01); *A61N 1/36064* (2013.01); *A61N 1/36067* (2013.01); *A61N 1/36071* (2013.01); *A61N 1/36075* (2013.01); *A61N 1/36078* (2013.01); *A61N 1/36082* (2013.01); *A61N 1/36089* (2013.01); *A61N 1/36096* (2013.01); *A61N 1/36103* (2013.01); *A61B 5/04* (2013.01); *A61N 1/36125* (2013.01); *A61N 1/36139* (2013.01); *A61N 1/3787* (2013.01); *A61N 1/37514* (2017.08)

(58) Field of Classification Search
 CPC .... A61N 1/375; A61N 1/3752; A61N 1/6864; A61N 1/6868; A61N 1/6882; A61N 1/3605; A61N 1/3606–36121; A61N 1/36146; A61N 1/3615; A61N 1/36153; A61N 1/36167; A61N 1/36171; A61N 1/36175
 See application file for complete search history.

(56) References Cited

U.S. PATENT DOCUMENTS

| | | | |
|---|---|---|---|
| 6,731,976 B2* | 5/2004 | Penn | A61B 5/0215 600/544 |
| 6,778,861 B1 | 8/2004 | Liebrecht et al. | |
| 6,920,359 B2 | 7/2005 | Meadows et al. | |
| 7,263,401 B2 | 8/2007 | Scott et al. | |
| 7,302,298 B2 | 11/2007 | Lowry et al. | |
| 7,346,391 B1 | 3/2008 | Osorio et al. | |
| 8,116,875 B2 | 2/2012 | Osypka et al. | |
| 8,504,166 B2 | 8/2013 | Lee et al. | |
| 8,718,777 B2* | 5/2014 | Lowry | A61N 1/0531 607/45 |
| 8,849,392 B2 | 9/2014 | Lozano | |
| 2012/0277812 A1 | 11/2012 | Kraus | |
| 2014/0094674 A1 | 4/2014 | Nurmikko et al. | |
| 2014/0276180 A1 | 9/2014 | Dextradeur et al. | |
| 2016/0184596 A1 | 6/2016 | Fried et al. | |

OTHER PUBLICATIONS

The National Institute of Mental Health, "Brain Stimulation Therapies", URL: http://www.nimh.nih.gov/health/topics/brain-stimulation-therapies/brain-stimulation-therapies.shtml 7 Pages total, (2016).

Roessler. K., et al., "Evaluation of Preoperative High Magnetic Field Motor Functional MRI (3 Tesla) in Glionia Patients by Navigated Electrocortical Stimulation and Postoperative Outcome", Journal of Neurology, Neurosurgery & Psychiatry, vol. 76, pp. 1152-1157, (2005).

Suess, O., et al, "Intraoperative Electrocortical Stimulation of Brodman Area 4: A 10-Year Analysis of 255 Cases", Head & Face Medicine, 23 Pages total. (Jul. 3, 2006).

* cited by examiner

SKULL IMPLANTED ELECTRODE ASSEMBLY FOR BRAIN STIMULATION

CROSS-REFERENCE TO RELATED APPLICATIONS

The present application is a divisional of U.S. application Ser. No. 15/277,589, filed Sep. 27, 2016, the entire contents of which are incorporated herein by reference.

BACKGROUND OF THE INVENTION

Technical Field

The present invention relates to an electronics assembly comprising an electrically-conductive cannulated screw configured to traverse a patient's skull to stimulate the patient's brain with an electric current, and methods of use.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Brain stimulation therapies involve activating or touching the brain directly with electricity, magnets, or implants to treat depression and other disorders. Electroconvulsive therapy is the most researched stimulation therapy and has the longest history of use. Other stimulation therapies discussed here—vagus nerve stimulation, deep brain stimulation, Ojemann direct cortical stimulation, and transcranial direct current stimulation—are newer, more experimental methods.

First developed in 1938, electroconvulsive therapy (ECT) for years had a poor reputation with many negative depictions in popular culture. However, the procedure has improved significantly since its initial use and is safe and effective. People who undergo ECT do not feel any pain or discomfort during the procedure.

ECT is usually considered only after a patient's illness has not improved after other treatment options are tried, such as antidepressant medication or psychotherapy. ECT is most often used to treat severe, treatment-resistant depression, but occasionally it is used to treat other mental disorders, such as bipolar disorder or schizophrenia. It also may be used in life-threatening circumstances, such as when a patient is unable to move or respond to the outside world (e.g., catatonia), is suicidal, or is malnourished as a result of severe depression. One study, the Consortium for Research in ECT, found an 86 percent remission rate for those with severe major depression. The same study found it to be effective in reducing chances of relapse when the patients underwent follow-up treatments.

Before ECT is administered, a person is sedated with general anesthesia and given a muscle relaxant to prevent movement during the procedure. An anesthesiologist monitors breathing, heart rate, and blood pressure during the entire procedure, which is conducted by a trained physician. Electrodes are placed at precise locations on the head, as in FIG. 1. Through the electrodes, an electric current passes through the brain, causing a seizure that lasts generally less than one minute.

Scientists are unsure how the treatment works to relieve depression, but it appears to produce many changes in the chemistry and functioning of the brain. Because the patient is under anesthesia and has taken a muscle relaxant, the patient's body shows no signs of seizure, nor does he or she feel any pain, other than the discomfort associated with inserting an IV.

Five to ten minutes after the procedure ends, the patient awakens. He or she may feel groggy at first as the anesthesia wears off. But after about an hour, the patient usually is alert and can resume normal activities.

A typical course of ECT is administered about three times a week until the patient's depression lifts (usually within six to 12 treatments). After that, maintenance ECT treatment is sometimes needed to reduce the chance that symptoms will return. ECT maintenance treatment varies depending on the needs of the individual, and may range from one session per week to one session every few months. Frequently, a person who undergoes ECT will take antidepressant medication or a mood stabilizing medication as well.

The most common side effects associated with ECT are headache, upset stomach, and muscle aches. Some people may experience memory problems, especially of memories around the time of the treatment. People may also have trouble remembering information learned shortly after the procedure, but this difficulty usually disappears over the days and weeks following the end of an ECT course. It is possible that a person may have gaps in memory over the weeks during which he or she receives treatment.

Research has found that memory problems seem to be more associated with the traditional type of ECT called bilateral ECT, in which the electrodes are placed on both sides of the head. Unilateral ECT, in which the electrodes are placed on just one side of the head-typically the right side because it is opposite the brain's learning and memory areas-appears less likely to cause memory problems and therefore is preferred by many doctors. In the past, a sine wave was used to administer electricity in a constant, high dose. However, studies have found that a brief pulse of electricity administered in several short bursts is less likely to cause memory loss, and therefore is most commonly used today ["Brain Stimulation Therapies," The National Institute of Mental Health, 2016; Berman, M., "A Tale of Two Carries: Bipolar Disease and Electroconvulsive Therapy," MedPage Today, 2013—each incorporated herein by reference in its entirety].

An ECT machine in common use is called the Somatics Thymatron System IV. Here are the parameters of the machine:

Peak current (mA): 900
Frequency (pulse pairs per second, pps): 10-140
Pulse width (ms): 0.25-1.5
Duration (sec): 0.1-8.0
Charge (mC): 25-504
Energy (J): 5-99

For instance, for a new patient receiving unilateral ECT, the energy is started at 5% energy (5 J). If no seizure occurs, the energy is increased to 10% (10 J). If again no seizure occurs, the energy is increased to 15% (15 J). If the patient has a seizure at 15%, then 90 J (i.e. six times 15 J) is used in the next treatment. For bilateral ECT, 1.5 times the seizure threshold energy is used, so in the above case, ~23 J would be used as the ECT energy.

Vagus nerve stimulation (VNS) works through a device implanted under the skin that sends electrical pulses through the left vagus nerve, half of a prominent pair of nerves that run from the brainstem through the neck and down to each side of the chest and abdomen. FIG. 2 shows an illustration of an implanted device for VNS. The vagus nerves carry messages from the brain to the body's major organs like the heart, lungs, and intestines, and to areas of the brain that control mood, sleep, and other functions.

VNS was originally developed as a treatment for epilepsy. However, it became evident that it also had effects on mood, especially depressive symptoms. Using brain scans, scientists found that the device affected areas of the brain that are also involved in mood regulation. The pulses also appeared to alter certain neurotransmitters (brain chemicals) associated with mood, including serotonin, norepinephrine, GABA, and glutamate.

In 2005, the U.S. Food and Drug Administration (FDA) approved VNS for use in treating major depression in certain circumstances—if the illness has lasted two years or more, if it is severe or recurrent, and if the depression has not eased after trying at least four other treatments. Despite FDA approval, VNS remains a controversial treatment for depression because results of studies testing its effectiveness in treating major depression have been mixed.

VNS works through a device called a pulse generator, which is about the size of a stopwatch, and is surgically implanted in the upper left side of the chest. Connected to the pulse generator is a lead wire, which is guided under the skin up to the neck, where it is attached to the left-side vagus nerve.

Typically, electrical pulses that last about 30 seconds are sent about every five minutes from the generator to the vagus nerve. The duration and frequency of the pulses may vary depending on how the generator is programmed. The vagus nerve, in turn, delivers those signals to the brain. The pulse generator, which operates continuously, is powered by a battery that lasts around 10 years, after which it must be replaced. Normally, a person does not feel any sensation in the body as the device works, but it may cause coughing or the voice may become hoarse while the nerve is being stimulated.

The device also can be temporarily deactivated by placing a magnet over the chest where the pulse generator is implanted. A person may want to deactivate it if side effects become intolerable, or before engaging in strenuous activity or exercise because it may interfere with breathing. The device reactivates when the magnet is removed.

VNS is not without risk. There may be complications such as infection from the implant surgery, or the device may become loose, move around, or malfunction, which may require additional surgery to correct. Long-term side effects are unknown.

Other potential side effects include voice changes or hoarseness, cough or sore throat, neck pain, discomfort or tingling in the area where the device is implanted, breathing problems (especially during exercise), and difficulty swallowing ["Brain Stimulation Therapies," The National Institute of Mental Health, 2016—incorporated herein by reference in its entirety].

Deep brain stimulation (DBS) was first developed as a treatment for Parkinson's disease to reduce tremor, stiffness, walking problems, and uncontrollable movements. In DBS, a pair of electrodes are implanted in the brain and controlled by a generator that is implanted in the chest, as illustrated in FIG. 3. Stimulation is continuous and its frequency and level is customized to the individual.

DBS has only recently been studied as a treatment for depression and obsessive compulsive disorder (OCD). Currently, it is only available on an experimental basis. So far, very little research has been conducted to test DBS for depression treatment, but the few studies that have been conducted show that the treatment may be promising. One small trial involving people with severe, treatment-resistant depression found that four out of six participants showed marked improvement in their symptoms either immediately after the procedure, or soon after. Another study involving 10 people with OCD found continued improvement among the majority three years after the surgery.

DBS requires brain surgery. The head is shaved and then attached with screws to a sturdy frame that prevents the head from moving during the surgery. Scans of the head and brain using MRI are taken. The surgeon uses these images as guides during the surgery. Patients are awake during the procedure to provide the surgeon with feedback, but they feel no pain because the head is numbed with a local anesthetic.

Once ready for surgery, two holes are drilled into the head. From there, the surgeon threads a slender tube down into the brain to place electrodes on each side of a specific part of the brain. In the case of depression, the part of the brain targeted is called Area 25. This area has been found to be overactive in depression and other mood disorders. In the case of OCD, the electrodes are placed in a different part of the brain believed to be associated with the disorder.

After the electrodes are implanted and the patient provides feedback about the placement of the electrodes, the patient is put under general anesthesia. The electrodes are then attached to wires that are run inside the body from the head down to the chest, where a pair of battery-operated generators are implanted. From here, electrical pulses are continuously delivered over the wires to the electrodes in the brain, usually to stimulate the sub-thalamic nuclei (STN), the globus pallidus (GPi), or the ventral intermedius nucleus (Vim) of the brain using these typical pulse parameters:

Typical Stimulation Parameters

| Parameter | STN | GPi | Vim |
| --- | --- | --- | --- |
| Amplitude (V) | 1.5-3.0-3.6 | 2.5-3.0-3.6 | 1.5-3.0-3.6 |
| Pulse width (µs) | 60-90 | 90-120 | 60-120 |
| Frequency (Hz) | 130-185 | 130-185 | 130-185 |

The electrodes may be in a unipolar configuration, which uses a single electrode or two or more adjacent electrodes with the same polarity. The electrodes may also be in a bipolar configuration in which two electrodes have different polarities.

Although it is unclear exactly how DBS works to reduce depression or OCD, scientists believe that the pulses help to reset the area of the brain that is malfunctioning so that it works normally again.

DBS carries risks associated with any type of brain surgery. For example, the procedure may lead to bleeding in the brain or stroke, infection, disorientation or confusion, unwanted mood changes, movement disorders, lightheadedness, and trouble sleeping.

Because the procedure is still experimental, other side effects that are not yet identified may be possible. Long-term benefits and side effects are unknown ["Brain Stimulation Therapies," The National Institute of Mental Health, 2016—incorporated herein by reference in its entirety].

Ojemann Direct Cortical Stimulation is used for intraoperative functional mapping with direct cortical-subcortical stimulation in patients who are awake. The method uses a stimulator (Ojemann Cortical Stimulator, Radionics) as in FIG. 4, to stimulate brain tissue with a bipolar probe with 5 mm spaced tips. Stimulation uses 60 Hz biphasic square wave pulses (1 ms/phase), with a progressive increase of the current amplitude (from 2 mA to 10 mA) until a motor and/or sensory response is obtained, or a language disturbance is induced. FIG. 5 shows an example of stimulating brain tissue with a bipolar Ojemann stimulator probe [Roessler, K., et al., Evaluation of preoperative high magnetic field motor functional MRI (3 Tesla) in glioma patients by navigated electrocortical stimulation and postoperative outcome. *J Neurol Neurosurg Psychiatry.* 2005, 76, 1152— incorporated herein by reference in its entirety].

Ojemann direct cortical stimulation carries similar risks associated with any type of brain surgery. For example, the procedure may lead to seizures, motor movement, disorientation or confusion, slurring or arrest of speech, and light-headedness.

Transcranial Direct Current Stimulation (tDCS) is a form of neurostimulation which uses constant, low current delivered directly to the brain area of interest via small electrodes. tDCS was originally developed to help patients with brain injuries such as strokes. Tests on healthy adults demonstrated that tDCS can increase cognitive performance on a variety of tasks, depending on the area of the brain being stimulated. tDCS has been utilized to enhance language and mathematical ability, attention span, problem solving, memory, and coordination.

Transcranial direct current stimulation works by sending constant, low direct current through electrodes. When these electrodes are placed in the region of interest, the current induces intracerebral current flow. This current flow then either increases or decreases the neuronal excitability in the specific area being stimulated based on which type of stimulation is being used. This change of neuronal excitability leads to alteration of brain function, which can be used in various therapies as well as to provide more information about the functioning of the human brain.

Transcranial direct current stimulation is a relatively simple technique and contains only a few parts. These include two electrodes and a battery powered device that delivers constant current. Control software can also be used in experiments that require multiple sessions with differing stimulation types such that neither the person receiving the stimulation nor the person administering the stimulation knows which type is currently being administered. Each device has an anodal electrode and a cathodal electrode. The anodal electrode is the positively charged electrode and the cathodal electrode is the negatively charged electrode. The current flows from the cathodal electrode to the anodal electrode, creating a circuit. The device that delivers the current has controls that set the current as well as the duration of stimulation.

To set up the tDCS device, the electrodes and the skin need to be prepared. This ensures a strong connection between the skin and the electrode. The careful placement of the electrodes is crucial to successful tDCS technique. The electrode pads come in various sizes with benefits to each size. A smaller sized electrode achieves a more focused stimulation of a site while a larger electrode ensures that the entirety of the region of interest is being stimulated. If the electrode is placed incorrectly, a different site or more sites than intended may be stimulated resulting in faulty results. One of the electrodes is placed over the region of interest and the other electrode, the reference electrode, is placed in another location in order to complete the circuit. This reference electrode is usually placed on the neck or shoulder of the opposite side of the body than the region of interest. Since the region of interest may be small, it is often useful to locate this region before placing the electrode by using a brain imaging technique such as fMRI or PET. Once the electrodes are placed correctly, the stimulation can be started. Many devices have a built-in capability that allows the current to be "ramped up" or increased slowly until the necessary current is reached. This decreases the amount of stimulation effects felt by the person receiving the tDCS. After the stimulation has been started, the current will continue for the amount of time set on the device and then will automatically shut off. Recently a new approach has been introduced where instead of using two large pads, multiple (more than two) smaller sized gel electrodes are used to target specific cortical structures. This new approach is called High Definition tDCS (HD-tDCS).

There are three different types of stimulation: anodal, cathodal, and sham. The anodal stimulation is positive (V+) stimulation that increases the neuronal excitability of the area being stimulated. Cathodal (V−) stimulation decreases the neuronal excitability of the area being stimulated. For example, cathodal stimulation might be used as a treatment for a psychological disorder caused by the hyper-activity of a particular area of the brain. Cathodal stimulation would decrease the neuronal excitability to reach a more stable level of activity. Sham stimulation is important because it is the control stimulation. This stimulation emits a brief current but then remains off for the remainder of the stimulation time. Without this type of stimulation, the effects of the positive or negative stimulation could not be proven. tDCS may be combined with magnetic stimulation in order to affect a patient's compound muscle action potentials, as illustrated in FIG. 6.

There are a few minor side effects that can be felt by the person while receiving the stimulation and most of these can be controlled by correct setup of the device. These side effects include skin irritation, a phosphene at the start of stimulation, nausea, headache, dizziness, and itching under the electrode. Nausea most commonly occurs when the electrodes are placed above the mastoid, which are used for stimulation of the vestibular system. A phosphene is a brief flash of light and this effect can occur if an electrode is placed near the eye. There are several ways to reduce the skin irritation felt during stimulation. One of the most important methods of preventing skin irritation is by preparing the electrodes with saline solution and the skin with electrode cream thoroughly. Also, ramping up the current can reduce the irritation. This is done by slowly increasing the current until the desired current is reached.

The market for neuro-technology products is poised to become one of the most dramatic growth areas of the 21st Century. Spurred on by medical developments and discoveries that cure disease, alleviate suffering, and generally improve the quality of life, many leading research institutions and healthcare firms have gained the world's attention and respect in recent years. Within biomedical technology, the field of neuro-technology stands out for its promise of restoring human brain function, and for transferring biomedical concepts and processes to the industrial and information processing sectors.

The fields of neuro-technology and neuroscience offer the promise of generating significant capital interest and funding, despite the current depressed state of new technology ventures. Investors will be looking for new opportunities in markets related to neuroscience. Neuro-technology, with its promise and proven record at such tasks as restoring hearing to deaf patients and hand function to quadriplegics, offers a clear opportunity.

In view of the forgoing, one objective of the present invention is to provide an implantable electrode assembly for stimulating a patient's brain with pulses of electric current.

BRIEF SUMMARY OF THE INVENTION

According to a first aspect, the present disclosure relates to an implantable electrode assembly that comprises an electrically-conductive cannulated skull screw with a head end and a point end. This skull screw is configured to transverse a patient's skull with the point end located at the interior surface of the skull and the head end at the exterior surface of the skull. The implantable electrode assembly also comprises an electronics module that has a casing, with the electronics module being electrically connected to the head end of the skull screw. The implantable electrode assembly also comprises a conductor housed in an insulated conduit and threaded through the skull screw. The conductor has a connection end and an electrode end, with the connection end located at the head end of the skull screw and electrically connected to the electronics module, and the electrode end configured to form an electrical connection with the patient's brain tissue.

In one embodiment, the electrode end of the conductor is configured to form at least two electrical connections with different locations of the patient's brain tissue.

In a further embodiment, the implantable electrode assembly also comprises a plurality of conductive discs housed within a flexible insulator with 1-20 mm spacing. The electrode end is electrically connected to the conductive discs to form at least two electrical connections with different locations of the patient's brain tissue.

In one embodiment, the implantable electrode assembly also has a photovoltaic power supply.

In another embodiment, the implantable electrode assembly also has a battery and a computer chip, and the exterior surface of the casing comprises one or more electrical contacts for linking to the battery and/or computer chip.

In another embodiment, the electronics module has at least one surface electrode configured to form an electrical connection with a scalp of a patient.

In one embodiment, the insulated conduit is removably attached to the head end of the skull screw by a key and keyhole mechanism, wherein the insulated conduit comprises a key and the head end of the skull screw comprises a complementary keyhole.

In a further embodiment, the insulated conduit comprises a triangular key and the head end of the skull screw comprises a complementary triangular keyhole.

In a further embodiment, the connection end of the conductor is removably attached to the electronics module by a key and keyhole mechanism.

In one embodiment of the implantable electrode assembly, the head end of the skull screw is removably attached to the electronics module by a key and keyhole mechanism.

In a further embodiment, where the head end of the skull screw is removably attached to the electronics module by a key and keyhole mechanism, the head end of the skull screw comprises a key and the electronics module comprises a complementary keyhole.

In a further embodiment, where the head end of the skull screw is removably attached to the electronics module by a key and keyhole mechanism, the electronics module comprises a key and the head end of the skull screw comprises a complementary keyhole.

In a further embodiment, where the electronics module comprises a key and the head end of the skull screw comprises a complementary keyhole for removable attachment, the electronics module further comprises a projection with an end that has an electrically-conductive spring-loaded piston. The projection and the electrically-conductive spring-loaded piston are configured to fit into a cavity in the head end of the skull screw and form a locked position with the skull screw and an electrical connection with the connection end of the conductor.

In one embodiment of the implantable electrode assembly, the insulated conduit is removably attached to the electronics module by a key and keyhole mechanism, wherein the insulated conduit comprises a key and the electronics module comprises a complementary keyhole.

In one embodiment of the implantable electrode assembly, the electronics module also has a wireless transceiver configured to receive a wireless signal encoding a program for brain stimulation and furthermore configured to send and receive a wireless signal with a portable wireless device.

According to a second aspect, the present disclosure relates to a method of treating a medical ailment of a patient with the implantable electrode assembly. The method involves implanting the implantable electrode assembly into a skull of the patient, forming an electrical connection with the patient's brain tissue and the electrode end of the conductor, and generating pulses of current between the electrode end of the conductor and the skull screw with pulse widths of 10 μs-300 ms, frequencies of 10-200 Hz, and voltages of 0.1-6 V. In this method, the medical ailment is epilepsy, migraine, depression, anxiety, attention deficit disorder, hyperactivity, bipolar disorder, stroke, dementia, schizophrenia, delirium, neurosis, psychosis, Parkinson's disease, alcohol withdrawal, drug withdrawal, dizziness, motion sickness, insomnia, dystonia, chronic pain, obsessive compulsive disorder, Tourette's syndrome, essential tremor, spasticity, trigeminal neuralgia, and/or headache.

In a further embodiment of the method, the electrode end of the conductor is configured to form at least two electrical connections with different locations of the patient's brain tissue, and the method further involves generating pulses of current between the at least two electrical connections with pulse widths of 10 μs-300 ms, frequencies of 10-200 Hz, and voltages of 0.1-6 V.

In one embodiment of the method, the method also involves removing the electronics module while leaving the conductor and cannulated skull screw in place and attaching a second electronics module.

According to a third aspect, the present disclosure relates to a method of monitoring a patient's brain activity with the implantable electrode assembly where the electrode end of the conductor is configured to form at least two electrical connections with different locations of the patient's brain tissue, and where the electronics module further comprises an on/off switch. The method of monitoring the patient's brain activity involves implanting the implantable electrode assembly into the patient's skull, connecting the electrode end with different locations of the patient's brain tissue, and turning on the electronics module with the on/off switch to receive electric activity between at least two electrical connections in the patient's brain.

In one embodiment of the method, the electronics module also has a digital storage medium and a wireless transceiver, and the method also involves converting the electric activity into a set of digital data, storing the set of digital data in the digital storage medium, and wirelessly transmitting the set of digital data with the wireless transceiver.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown.

According to a first aspect, the present disclosure relates to an implantable electrode assembly that comprises an electrically-conductive cannulated skull screw with a head end and a point end. This skull screw is configured to transverse a patient's skull with the point end at the interior surface of the skull and the head end at the exterior surface of the skull. The implantable electrode assembly also comprises an electronics module that has a battery, a computer chip, and a casing, with the electronics module being electrically connected to the head end of the skull screw. The implantable electrode assembly also comprises a conductor housed in an insulated conduit and threaded through the skull screw. The conductor has a connection end and an electrode end, with the connection end located at the head end of the skull screw and electrically connected to the electronics module, and the electrode end configured to form an electrical connection with the patient's brain tissue.

Figure 7A:
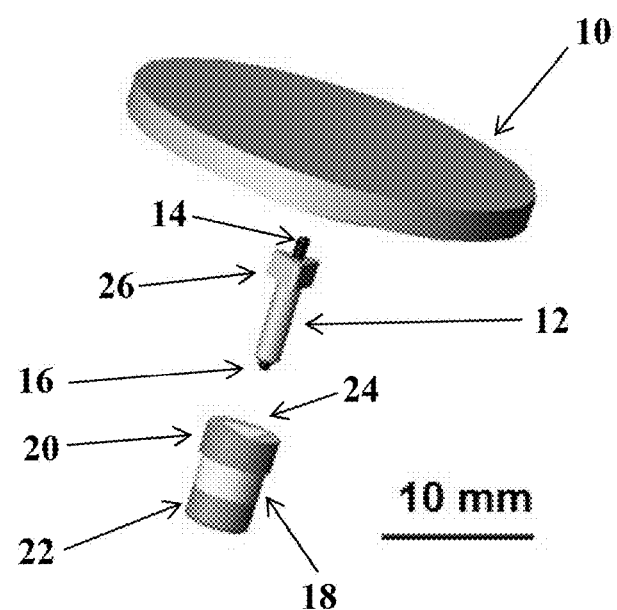
FIG. 7A is an example of an implantable electrode assembly.
Figure 7B:
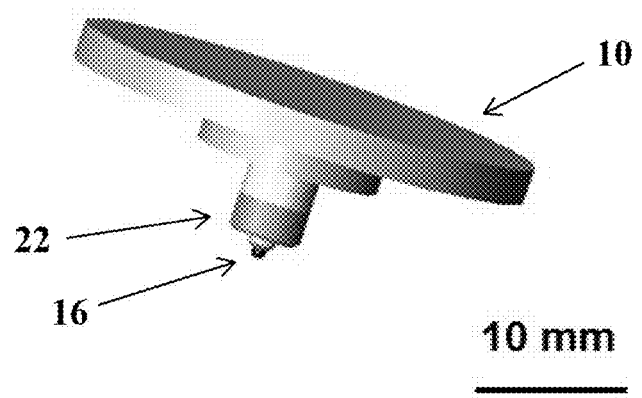
FIG. 7B shows the assembled implantable electrode assembly of FIG. 7A.

FIG. 7A shows a diagram of an implantable electrode assembly, comprising an electronics module 10 housed in a casing, a conductor housed in an insulated conduit 12, with the conductor having a connection end 14 and an electrode end 16, and a cannulated skull screw 18 with an electrically-conductive head end 20 and point end 22. FIG. 7B shows the same implantable electrode assembly in an assembled state.

In one embodiment, the exterior of skull screw may be comprised of an electrically-conductive material such as platinum, platinum-iridium alloy, iridium, titanium, titanium alloy, stainless steel, gold, cobalt alloy and/or some other biocompatible electrically-conductive material. Preferably, the skull screw may be comprised of platinum or stainless steel. As defined here, a "conductive material" is a substance with an electrical resistivity of at most $10^{-6}$ Ω·m, preferably at most $10^{-7}$ Ω·m, more preferably at most $10^{-8}$ Ω·m at 20° C. In an alternative embodiment, the exterior of the skull screw may comprise a non-conductive biocompatible material, such as carbon fiber, polyethylene, polymethylmethacrylate, polyether ether ketone, and/or polycarbonate, but also comprise a region of a conductive material, either formed into the exterior surface of the screw or as an electrode attached along its side, so that the skull screw may be electrically-conductive. In one embodiment, the screw may be formed of one material, such as the previously-listed metals and non-metals, or a combination thereof, and then coated or electroplated with platinum. In a related embodiment, the thread of the screw may be stainless steel or platinum, while the rest of the screw may be a different material. In another related embodiment, the midsection of the screw's exterior may be electrically insulated, but with the head end of the screw electrically connected to the point end of the screw. For example, FIG. 7A shows a skull screw 18 with the exterior surface of the midsection being insulated, yet with the head end 20 being electrically connected to the point end 22. In one embodiment, the skull screw comprises materials that can withstand sterilization by autoclaving.

In one embodiment, the screw is cannulated, which means that it has a hollow core through its entire length. The hollow core may be cylindrical, square, or some other shape, such as a cylinder with a groove. Preferably the hollow core is cylindrical with a diameter 0.75-8.75 mm, preferably 1-8 mm, more preferably 2-7 mm. In one embodiment, the shape of the hollow core may vary throughout the length of the skull screw. For example, the hollow core may narrow towards the point end of the screw. Alternatively, a cylindrical hollow core may have two or more sections with different diameters.

Figure 8:
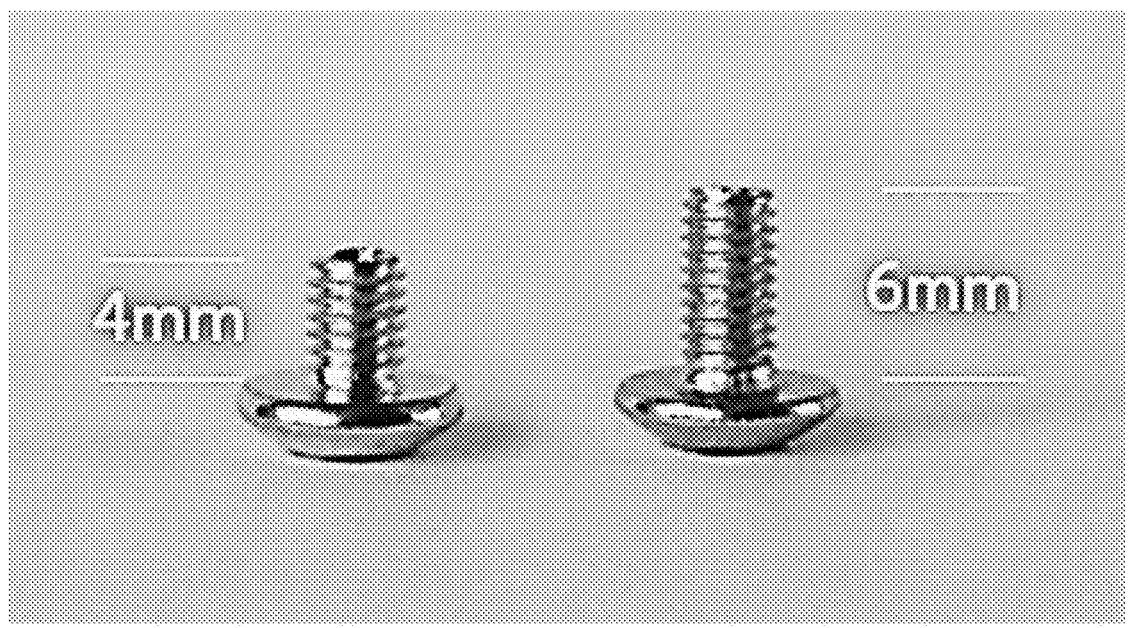
FIG. 8 shows an example of skull screws.

In one embodiment, the skull screw may comprise along its length an unthreaded head section and a shaft section, wherein the unthreaded head section is located near the head end, and the shaft section starts from the point end and may be fully or partially threaded. The unthreaded head section may have a length less than 50%, preferably less than 40%, more preferably less than 30% of the total shaft length, with the remainder length as the shaft section. FIG. 8 shows skull screws with completely threaded shaft sections of 4 mm and 6 mm in length. In the embodiment where the shaft section is partially threaded, there may be a threaded section starting from the point end and an unthreaded section between the threaded section and the unthreaded head section. The unthreaded section may comprise less than 50%, preferably less than 20%, more preferably less than 10% of the length of the shaft. In one embodiment, the shaft is completely threaded. The shaft may be cylindrical, or conical with a taper towards the point end. The core diameter, which is the smallest diameter of the threaded section, may be 0.5-9 mm, preferably 0.8-8 mm, more preferably 1-7 mm. The thread diameter, which is the widest diameter of the threaded section, may be 1-10 mm, preferably 1.2-9 mm, more preferably 1.5-8 mm. The shaft section diameter may be 0.5-9 mm, preferably 0.8-8 mm, more preferably 1-7 mm. The core diameter may vary along the length of the shaft section. For example, the core of the screw may be conical while the threaded diameter is cylindrical.

The thread of the screw may be single or double start and may be right-handed or left-handed. The design of the screw thread may allow for an implanted screw to be self-locking, self-tapping, and/or self-drilling. In a preferred embodiment, the skull screw may have a lower pullout strength compared to a conventional bone and/or skull screw. The shape of the screw threads may be V, American National, British Standard, buttress, Unified Thread 1o Standard, ISO metric, or some different shape known to those of ordinary skill. The pitch of the thread may be 0.1 mm-1 mm, preferably 0.2-0.9 mm, more preferably 0.2-0.8 mm. The point end of the skull screw may be flat, curved, or beveled towards the opening of the hollow core, or may be some other shape. For example, FIGS. 7A, 7B, and 8 show screws with flat ends, while FIGS. 9, 13A, 13B, 14, 15, and 17 show screws with beveled ends.

In one embodiment, the skull screw shaft section may comprise at least two threaded sections separated by an unthreaded section. The at least two threaded sections may have the same dimensions or they may differ in length, thread diameter, and/or core diameter. In one embodiment, at least two threaded sections are adjacent on the shaft section and differ by thread diameter, and/or core diameter. Alternatively, the shaft section may comprise at least two unthreaded sections separated by a threaded section.

Where a skull screw comprises an unthreaded head section, the widest diameter of the unthreaded head section may be greater than the core diameter of the screw by more than 1 mm, preferably more than 2 mm, more preferably more than 2.5 mm. In alternative embodiments, the widest diameter of the unthreaded head section may be equal to or less than the core diameter, for example, the widest diameter of the unthreaded head section may be smaller than the core diameter by 2.5 mm or less, preferably 2 mm or less, more preferably 1 mm or less. The unthreaded head section of the skull screw may be shaped cylindrically, or may be a right prism with a regular polygonal base such as a square, a hexagon, or octagon, or it may be some other shape, such as a sphere or hemisphere.

Preferably the top of the skull screw head end is located at least 3 mm, preferably at least 4 mm, more preferably at least 5 mm above the scalp of the patient. Preferably, any contact by the point end of the skull screw does not harm the brain tissue. In an alternative embodiment, the skull screw is inserted sufficiently deep that the top of the skull screw head end is at the same level as the patient's skull or scalp, or between those two levels.

The skull screw may be threaded with a conductor housed in an insulated conduit. An insulated conduit is comprised of an insulator placed on at least one exterior surface of a conduit. Defined here, an insulator refers to a solid material with a high electrical resistivity that may prevent an electric current from flowing between two points. The electrical resistivity of the insulator may be at least $10^2$ Ω·m, preferably at least $10^3$ Ω·m, more preferably at least $10^4$ Ω·m at 20° C. The insulator may comprise polytetrafluoroethylene (PTFE), polyvinylchloride (PVC), polyethylene terephthalate (PET), polyethylene (PE), polylactic acid (PLA), poly (lactic-co-glycolic acid) (PLGA), acrylonitrile butadiene styrene (ABS), silicone, silicon dioxide, ceramic, or any combination thereof. The conductor may be a flexible or rigid conductive material with an electrical resistivity as defined previously. The conductor may comprise additional conductive materials such as copper, aluminum, nickel, steel, and/or iron. In an alternative embodiment, where the interior surface of the hollow core of the skull screw comprises an insulating material, the conductor may thread directly through the skull screw.

Figure 9:
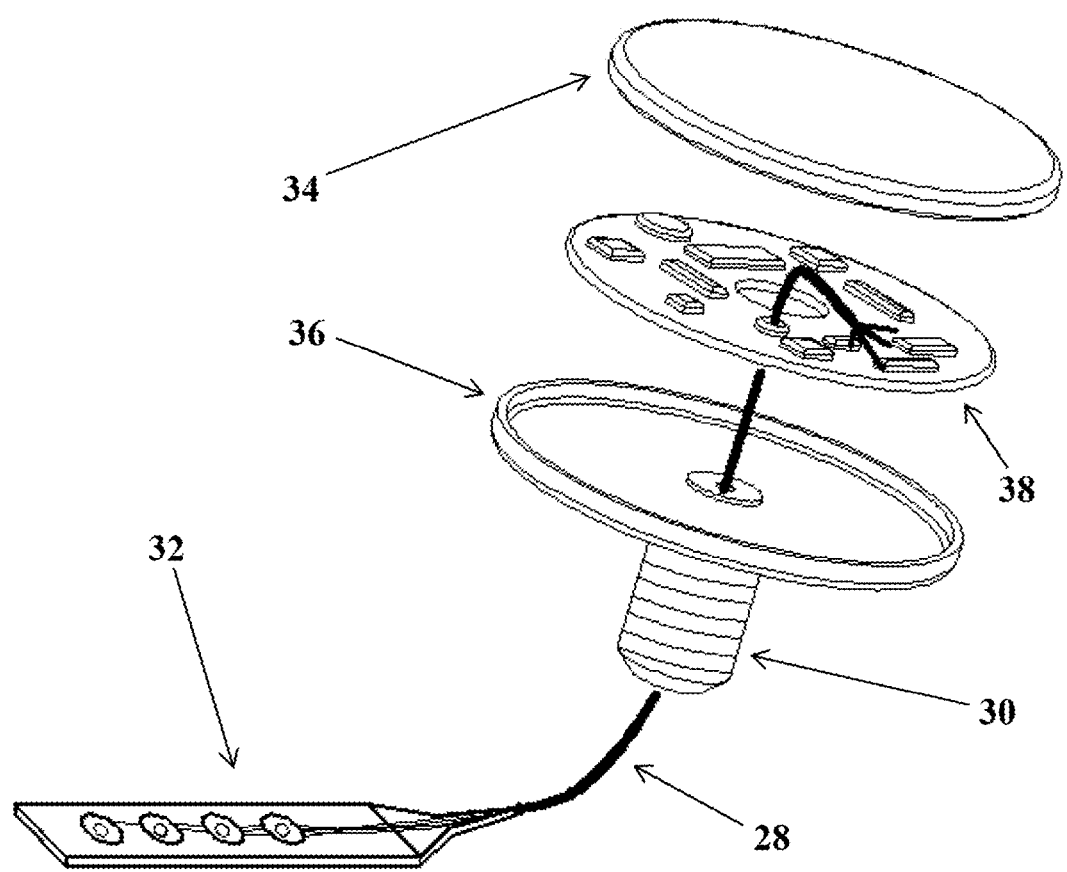
FIG. 9 is an illustration of an implantable electrode assembly that comprises multiple electrode contacts housed in a flexible, insulated conduit.
Figure 10:
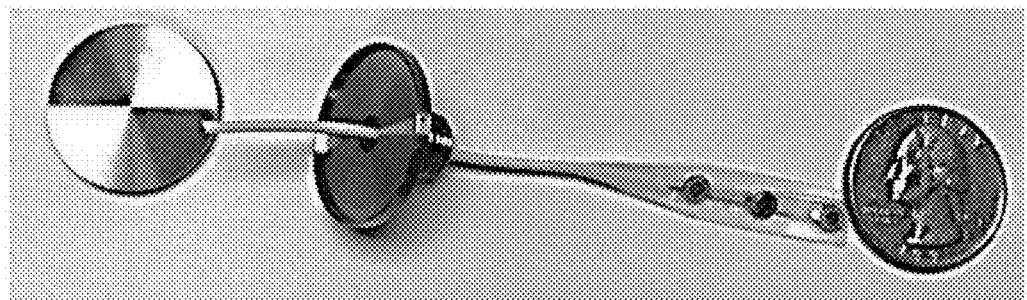
FIG. 10 is a model of FIG. 9 shown next to a U.S. quarter dollar for size comparison.

The cross-section area of the insulated conduit may be equal to or less than the cross-section area of the hollow core of the skull screw, and shaped so that it can be inserted through its length. Preferably the length of the insulated conduit is greater than the length of the skull screw, and the insulated conduit is threaded through such that the electrode end of the conductor is physically separated from the point end of the skull screw by at least 0.5 mm, preferably at least 0.8 mm, more preferably at least 1 mm. The insulated conduit may not be fixed within the skull screw, allowing it to rotate or move up or down within the skull screw, or it may be fixed by an adhesive or by an attachment at the connection end of the conductor. In one embodiment, the insulated conduit is significantly longer than the length of the skull screw so that the electrode end of the conductor is separated by at least 4 cm, preferably at least 6 cm, more preferably at least 8 cm. FIG. 9 illustrates an implantable 1o electrode assembly with a flexible insulated conduit 28 threaded through the cannulated skull screw 30. FIG. 10 is a photograph of a similar model.

The conductor may be housed in the insulated conduit so that the insulated conduit covers all but the electrode end and the connection end of the conductor. The electrode end of the conduit and the connection end of the conduit may thus be electrically connected. In one embodiment, the conductor forms just one electrical connection between one point of the electrode end and one point of the connection end. In that embodiment, the conductor may comprise a flexible braided wire of 2-10 strands, but preferably the conductor is a single wire. The gauge of the wire or wires may be 0-40 AWG, preferably 1-38 AWG, more preferably 4-34 AWG. In one embodiment, the wire or wires may be shielded. FIG. 7A is an example embodiment where the conductor forms a single electrical connection between the electrode end and the connection end.

In one embodiment, the electrode end of the conductor is configured to form at least two electrical connections with different locations of the patient's brain tissue. These may be equal distances from the tip end of the skull screw, or different distances. In another embodiment, the conductor may form two or more electrical connections at the electrode end, and/or two or more electrical connections at the connection end, which may be accomplished by an insulated conduit that further insulates two or more wires from each other. The conductor may comprise a single wire, or a bundle of wires. Where the conductor comprises a bundle of wires, each wire may be electrically insulated from each other or some wires may form electrical connections with each other. In one embodiment, the electrode end of the conductor may comprise a different conductive material than that housed in the insulated conduit. For example, the insulated conduit may house a copper wire that is electrically connected to a platinum conductor. In one embodiment, the conductor is a wire or wires, and the end of the wire or wires is the electrode end. Alternatively, the wire or wires at the electrode end may comprise conductive material in a different form, such as discs, rods, cubes, spheres, or some other shape, with a largest dimension of 0.1-4 mm, preferably 0.1-3 mm, more preferably 0.2-2.5 mm, and may comprise the same conductive material of the wire or a different conductive material. Preferably, the wire or wires of the electrode end terminate as wires or discs that comprise platinum, platinum-iridium alloys, iridium, and/or stainless steel. The surfaces of the conductive materials at the electrode end may be modified to change their charge transfer properties. For example, platinum may be roughened by laser patterning. The electrode end of the conductor forms an electrical connection with a patient's brain tissue when the combined electrode end and tissue are in physical contact and form a conductive material with an electrical resistivity as defined previously. In an alternative embodiment, the electrode end of the conductor may comprise one or more electromagnets for stimulating a patient's brain with pulses of magnetic fields.

Figure 11:
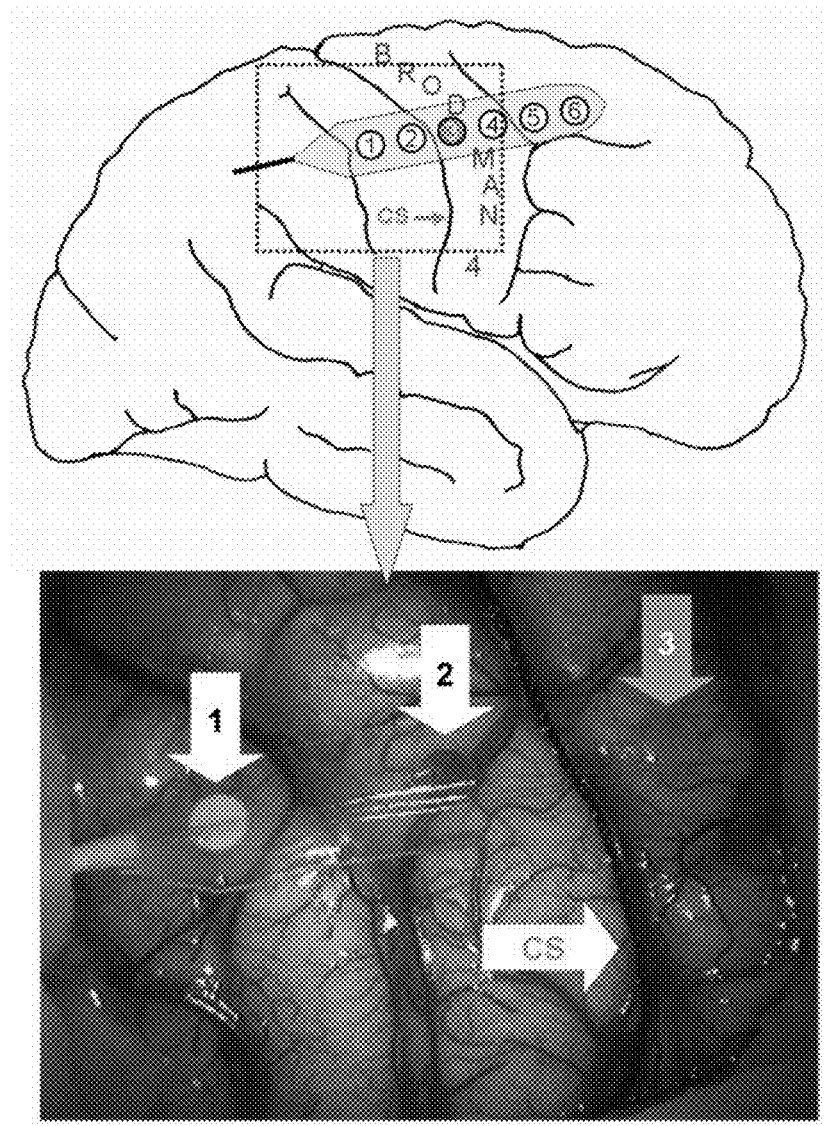
FIG. 11 is an example of cortical brain stimulation using multiple electrode contacts housed in a flexible, insulated conduit.

In a further embodiment, the implantable electrode assembly also comprises a plurality of conductive discs housed within a flexible insulator with a spacing of 1-20 mm, preferably 2-15 mm, more preferably 4-12 mm. The electrode end is electrically connected to the conductive discs to form at least two electrical connections with different locations of the patient's brain tissue. These conductive discs may have a diameter of 0.1-5 mm, preferably 0.1-4 mm, more preferably 0.2-3 mm, with an exposure diameter of 0.1-4.5 mm, preferably 1-3.5 mm, more preferably 1.5-3 mm. Alternatively, the flexible insulator may comprise other forms of conductive material such as those mentioned previously. The conductive discs may be arranged linearly with equal spacing for a total length of 2.5-12 cm, preferably 3-10 cm, more preferably 3.5-9 cm. FIG. 9 shows an illustration of an implantable electrode assembly with a linear array of conductive discs housed in a flexible insulator 32, and FIG. 10 shows a photograph of a similar model. FIG. 11 shows an example of such a flexible insulator forming electrical connections with a patient's brain tissue for conical stimulation. Here, a linear array of six conductive discs is placed on a patient's cortex with disc #3 being placed directly on Broadman Area 4 for its electrical stimulation. CS denotes the central sulcus [Suess, O., et al., Intraoperative electrocortical stimulation of Brodman area 4: a 10-year analysis of 255 cases, *Head & Face Medicine*. 2006, 20—incorporated herein by reference in its entirety]. Alternatively, the conductive discs may be arranged linearly with unequal spacing. In one embodiment, the conductive discs are arranged on a curve, and in another embodiment, the conductive discs are arranged in a 2D array. The flexible insulator housing the conductive discs may comprise or be made of polytetrafluoroethylene (PTFE), polyvinylchloride (PVC), polyethylene terephthalate (PET), polyethylene (PE), polylactic acid (PLA), poly(lactic-co-glycolic acid) (PLGA), silicone, or some other flexible, biocompatible polymeric insulating material. Preferably, each conductive disc is wired independently and electrically isolated from any other conductive disc, however, in one embodiment, two or more conductive discs may be wired together. In one embodiment, the flexible insulator housing the conductive discs further comprises conductive wires for forming additional electrical connections with a patient's brain tissue. Preferably the conductive discs comprise platinum, platinum-iridium alloys, iridium, and/or stainless steel.

In one embodiment, the implantable electrode assembly has an electronics module housed in a casing and that forms separate electrical connections with the head end of the skull screw and with the connection end of the conductor. An electrically-conductive material as a strip, button, spring, pin, piston, or other shape on a side of the electronics module closest to the patient's head may form an electrical connection between the head end of the skull screw and the electronics module. The electrical connection on the head end of the skull screw may be formed on an exterior side of the skull screw, such as on an unthreaded head section, on the top of the head end, or just inside the hollow core of the skull screw, for example, by locating an electrically-conductive strip between the insulated conduit and the hollow core. In another embodiment, a sliding tab on the casing of the electronics module may form an electrical connection with the head end of the skull screw. Preferably, however, attaching the skull screw to the electronics module is sufficient to form the separate electrical connections of the screw and the conductor to the electronics module. The connection end of the conductor may form an electrical connection with the electronics module by contacting an electrically-conductive material in any of the previously mentioned shapes.

In one embodiment, the electronics module further comprises a casing. The casing may have a width or diameter of 8-130 mm, preferably 13-70 mm, more preferably 15-50 mm, and a height of 4-110 mm, preferably 6-40 mm, more preferably 6-20 mm. The casing may be rectangular, triangular, disc-shaped, or some other shape. Preferably the casing is disc-shaped. The casing may be any of the previously mentioned materials suitable for the skull screw, or the casing may be another metal such as nickel and/or aluminum, or another polymeric material such as polylactic acid (PLA), poly(lactic-co-glycolic acid) (PLGA), polyethylene terephthalate (PET), acrylonitrile butadiene styrene (ABS), and/or polytetrafluoroethylene (PTFE), or some other nonmetal, such as glass or ceramic. In the embodiment where the casing comprises a conductive material, preferably the casing is kept electrically isolated from the skull screw and the electrical components of the electronics module. Alternatively, the casing may be made of an insulating material. In one embodiment, the casing of the electronics module is about the size of a quarter dollar of United States currency, as shown by the model in FIG. 10, meaning that the casing may have a diameter of 20-28 mm and a thickness of 1.7-10 mm. In addition, the top of the casing may be smoothed to reduce edges and decrease the likelihood of the casing catching on clothing, hats, or helmets.

In one embodiment, the casing may include a cushion on a part of the casing that contacts a patient's head. The part of the casing in contact with a patient's head may entirely comprise a cushion, or only a portion may comprise a cushion, for example, in the form of raised ridges or bumps. Alternatively, the entire exterior surface of the casing, including surfaces that are not in contact with a patient's head, may comprise a cushion. The cushion may comprise an elastomeric compound such as silicone rubber, latex, butyl rubber, neoprene, and/or nitrile, and may be solid or comprise air pockets. The cushion may have a height or thickness of 1 mm-4 mm, preferably 1.5-3 mm, more preferably 1.6-2 mm.

In another embodiment, the exterior surface of the casing comprises a tab portion, a notch, or a textured surface to facilitate a finger grip. A tab may be in the form of a projection on the surface of the casing while a notch may be in the form of a V-shaped cut. The exterior surface of the casing may be textured with grooves, bumps, knurls, ridges, and/or ribs. A tab, notch, or textured feature may be present in any combination or number on any exterior surface of the casing not in contact with a patient's head. In one embodiment, to facilitate a finger grip, the casing is covered with a cushion of an elastomeric material, such as those listed previously.

In one embodiment, the skull screw and a bottom portion of the casing are machined from a single piece of material. To provide access to the battery and/or interior of the electronics module, a top portion of the casing may be removably attached to the bottom portion. FIG. 9 illustrates a top portion 34 of the casing being separated from a bottom portion 36 of the casing, which together houses the electronics module 38. The skull screw 30 and bottom portion of the casing 36 may be machined from a single piece of metal. FIG. 10 shows a photograph of a similar model with the top portion of the casing removed.

Figure 14:
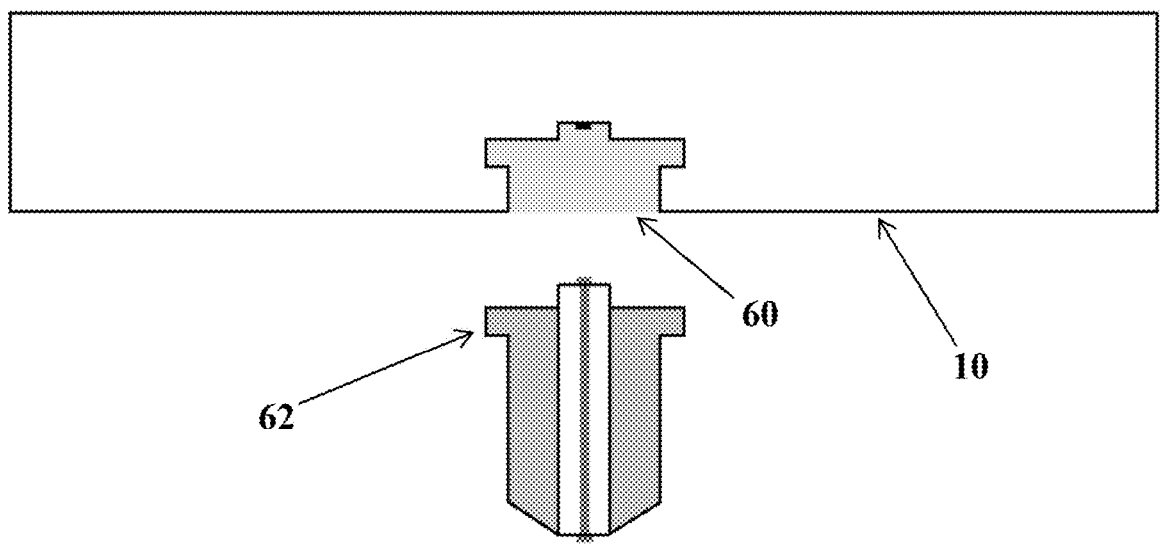
FIG. 14 shows a cross-section view of an implantable electrode assembly where the head end of the skull screw functions as a key and the electronics module functions as a keyhole in order to removably attach the two.

In one embodiment, the casing may not be entirely flat, but curved to the shape of a person's head. It is possible that once a skull screw location has been determined, a customized casing may be fabricated to better fit the local curve of a patient's head. Likewise, in one embodiment, the casing may comprise an indentation in a central portion of diameter 2.5-12 mm, preferably 5.5-11 mm, more preferably 6-9.5 mm on the side closest to a patient's head in order to receive the skull screw. This indentation may allow the casing to sit on the surface of a patient's scalp. Alternatively, in the embodiment where the entire implantable electrode assembly is located beneath a patient's scalp, the indentation may allow the casing to sit on the surface of a patient's skull. The indentation may be about the size of an unthreaded head section of a skull screw, or the portion of a skull screw that protrudes above a patient's scalp or skull. The indentation depth may be 1-10 mm, preferably 2-8 mm, more preferably 3-7 mm. The indentation may go through the bottom portion of the casing partway, or it may go through entirely as a hole in the casing that exposes the interior of the electronics module. In another embodiment, the interior sides of the indentation may form a fastening mechanism to removably attach to the head end of the skull screw. For example, FIG. 14 shows an indentation 60 in the casing of the electronics module 10 that forms a keyhole attachment mechanism with the head end 62 of the skull screw.

In one embodiment, the electronics module comprises a battery and a computer chip. The battery may comprise one or more electrochemical cells of alkaline, lithium, lithium-ion, nickel-cadmium, nickel metal hydride, zinc-air, silver oxide, and/or carbon-zinc. The electrochemical cells may be wired in parallel, in series, or a combination of both. Preferably the battery is rechargeable. The battery may have a nominal capacity of 10-1500 mAh, preferably 20-1100 mAh, more preferably 30-700 mAh. A single electrochemical cell may be housed in its own battery casing, such as a round button cell, or may be housed in a battery casing with one or more other cells. The battery casing that houses one or more cells may be rectangular, disc-shaped, rod-shaped, or in some other shape. Preferably the battery is a round button cell with a diameter of 5-40 mm, preferably 9-30 mm, more preferably 10-25 mm, and with a height of 1-12 mm, preferably 1.5-8 mm, more preferably 2-5 mm. In one embodiment, the battery is about the size of a watch battery, meaning that the battery is a disc with a diameter of 19-21 mm and a thickness of 1.5-2.7 mm. In an alternative embodiment, the computer chip and optionally other electronics are housed in the casing but the battery is housed in a separate casing. In this embodiment, the battery may be larger and possess a greater nominal capacity.

The computer chip of the electronics module is electrically connected to the battery, the connection end of the conductor, and to the head end of the skull screw. The computer chip may have the ability to digitize electric signals received at the skull screw and the connection end of the conductor. The computer chip may also be able to monitor the capacity of the battery.

In one embodiment, the electronics module further comprises a pulse generator. Here, the computer chip may be able to deliver pulse parameters to the pulse generator, and the pulse generator may receive power from the battery to send the pulses of current to the head end of the skull screw and/or the electrode end of the conductor. Through the pulse generator, the computer chip may be able to control the pulse shape, the pulse frequency, the pulse width, the pulse voltage, and the direction of current. The pulse generator may be able to generate square, sine wave, Gaussian, and other pulse shapes with frequencies of 10 Hz-1 kHz, pulse widths of 10 µs-1 s, and voltages of 0.1-6 V with direct or alternating current. In the embodiment where the electrode end of the conductor forms a single electrical connection with a patient's brain tissue, the pulse generator may direct current in the direction to make the electrode end the cathode and the skull screw point end the anode. Alternatively, the pulse generator may direct current in the reverse direction, with the electrode end as the anode and the point end as the cathode. In a further embodiment, the pulse generator may send alternating current between the point end and the electrode end. In the embodiment where the electrode end of the conductor is configured to form at least two electrical connections with different locations of a patient's brain tissue, the pulse generator may send current to or from the skull screw point end and any one of the electrical connections. Alternatively, the pulse generator may send current between individual electrical connections. In the embodiment where the electrode end of the conductor has three or more electrical connections, at least one electrical connection may be inactive while the pulse generator sends or receives current from the other electrical connections. In another embodiment with three or more electrical connections, the pulse generator may actively send and/or receive current from all electrical connections.

In one embodiment, the electronics module further comprises a digital storage medium. This digital storage medium may be able to store a program for electric stimulation and/or digital data about electric activity received from the head end of the skull screw and/or the electrode end of the conductor. A program for electric stimulation may include pulse parameters and the duration of the electric stimulation. In some cases, the pulse parameters may change within a single electric stimulation session, for example, the pulse widths may broaden. A program stored in the digital storage medium may be transferred to the computer chip's memory, and the computer chip may control the pulse generator based on the program.

In one embodiment, the electronics module may comprise a photovoltaic power supply. This may be a photovoltaic solar cell mounted to the exterior of the casing. The photovoltaic power supply may be able to charge the battery of the electronics module when the implantable electrode assembly is not delivering pulses or receiving electric activity. In one embodiment, the photovoltaic power supply may be able to circumvent the battery and directly power the implantable electrode assembly.

In one embodiment, the electronics module may further comprise a wireless transceiver, which can send and/or receive a wireless signal encoding digital data with a portable wireless device. The digital data may be a program, in which case the wireless transceiver receives the wireless signal and converts it to digital data which is sent to the computer chip and stored in the digital storage medium. Likewise, the computer chip may be able to retrieve a program from the digital storage medium and send it to the wireless transceiver for wireless signal encoding and transmission. Alternatively, the digital data may be a recording of electric activity of a patient's brain, and stored in the digital storage medium. Here, the computer chip may retrieve the digital data and send it to the wireless transceiver for wireless transmission as described above. The wireless transceiver may also be able to receive a wireless signal encoding a recording of a patient's brain activity destined for storage in the digital storage medium. The wireless transceiver may comprise an interior antenna, or may attach to an exterior antenna. The transceiver may use an established wireless transmission protocol such as 802.11x, CDMA, IS-136, Bluetooth, Bluetooth low energy, Ultra-wideband, GSM, 6LoWPAN, 802.15.4, ANT, DASH7, ISA100.11a, MiWi, near-field communication, OCARI, ONE-NET, TSMP, WirelessHART, ZigBee and/or Z-Wave, or may use some other wireless transmission means. The portable wireless device may be a cell phone, a tablet computer, a laptop computer, a portable amateur radio, or some other wireless controller.

The wireless transceiver may also be able to send and receive wireless signals encoding other information, such as battery status and/or software updates. In one embodiment, the wireless transceiver can send and receive signals with another implantable electrode assembly or with a desktop computer or cell phone tower. In one embodiment, the wireless transceiver can join a wireless network and connect with other computers or devices remotely through the Internet or some other network.

In one embodiment, the digital data transferred to or from the wireless transceiver may comprise more than one program for brain stimulation and/or more than one recording of electric activity.

In one embodiment, the exterior surface of the casing comprises one or more electrical contacts for linking to the battery and/or computer chip. These electrical contacts may be in the form of pins, screws, binding posts, springs, rings, USB connectors, coaxial power plugs, phone connectors (2.5, 3.5, or 6.35 mm), Molex connectors, FireWire connectors, banana connectors, Tamiya connectors, JST connectors, SAE connectors, registered jack (RJ) connectors, Anderson Powerpole connectors, EIAJ connectors, DIN connectors, blade connectors, crimp connectors, or other plug and socket connectors. An electrical contact to the battery may allow for recharging the battery, and an electrical contact to the computer chip may allow for the transfer of digital data, for example, sending and/or retrieving programs and/or recordings of brain activity. The battery may be charged while the electronics module is attached to a patient's head, or it may be charged after detaching the electronics module from a patient's head. In a related embodiment, where the electronics module comprises a wireless transceiver, the exterior surface may have an electrical contact for attaching an exterior antenna. In an alternative embodiment, a power source may be attached to an exterior electrical contact on the casing to directly power the electronics module. For instance, this power source may be an exterior battery, a photovoltaic cell, or an AC adaptor. In an alternative embodiment, the electronics module may comprise a coil for charging the battery by induction. In another alternative embodiment, the electronics module or an exterior surface of the casing may comprise an antenna for charging the battery through radio waves.

In one embodiment, the electronics module further comprises an on/off switch, which may be present on an exterior surface of the casing. The on/off switch may work by breaking the circuit between the battery and the computer chip, and may be a button or a switch. In one embodiment, the on/off switch is built into the fastening mechanism between the skull screw and the electronics module, so that, for example, rotating the electronics module relative to the skull screw turns it on or off. In one embodiment, the exterior surface of the casing may comprise an indicator light that shines when the on/off switch is in the "on" position. Alternatively, the casing may have one or more indicator lights, each with an ability to emit light of more than one color. For example, with the switch in the "on" position, one color may shine when the battery has a capacity of greater than 10% of its charged capacity, and another color may shine when the capacity is 10% or less. Alternatively, the indicator light may blink to indicate battery status. In one embodiment, the electronics module may comprise a wireless transceiver, but no on/off switch. In that embodiment, the electronics module may exist in a low-power state until receiving a certain wireless signal to activate it to a full-power state. In a related embodiment, the electronics module may be turned on or off with a magnet or by inductive coupling, for instance, with a portable electronic device. In one embodiment, the electronics module may be able to turn itself off without the on/off switch, for example, after a set time period or after no longer receiving brain activity from the electrode end and/or skull screw.

In one embodiment, the electronics module has at least one surface electrode configured to form an electrical connection with a scalp of a patient. This surface electrode may be attached to the electronics module through an electrical contact on the exterior surface of the casing. The surface electrode may form an electrical connection with a patient's scalp, forehead, temple, neck, jaw, cheekbone, or other location and allow for transdermal electrical stimulation of the brain. More than one surface electrode may be connected to the electronics module. The surface electrode or electrodes may be used with the implanted electrodes for brain stimulation, or both types of electrodes may be used separately. Similarly, the surface electrode or electrodes may record brain activity of a patient in tandem with the implanted electrodes, or the recording may be performed separately. The surface electrodes may attach to the patient by clips or adhesive, and may use an adhesive, a salt paste or gel, or a wet sponge to form an electrical connection to that part of the patient's scalp or skin. In one alternative embodiment, the surface electrodes are placed around the scalp in locations to record an electroencephalogram. In another alternative embodiment, the electrodes are placed on a patient's limbs and chest in order to record an electrocardiogram.

In one embodiment, the electronics module and the skull screw are removably attached. In detaching the two, the insulated conduit may remain attached to the electronics module or to the skull screw. Preferably, the casing can be attached or detached from a skull screw implanted in a patient's head without changing the positioning of the skull screw and without causing discomfort to the patient. In one embodiment, this fastening mechanism may be a bayonet mount, magnets, a threaded connector, a clutch, a latch, a key and keyhole, a tongue and groove joint, a snap fastener, an R-clip, a clamp, or any combination thereof. The fastening mechanism may comprise additional parts such as pins, springs, tabs, or levers. In one embodiment, the electronics module, skull screw, and insulated conduit are all removably attached from one another. For example, the electronics module and the conductor housed in the insulated conduit may together be separated from the skull screw, and then the electronics module and the conductor may be separated from each other, as in FIG. 13B. Where an implantable electrode assembly comprises two or more attachment mechanisms, the attachment mechanisms may be the same type or different types.

As used herein, a "key and keyhole" refers to a removable attachment mechanism that joins two parts: one part comprises an elongated member ("key") with a shape on its end, and a second part which comprises a cavity located behind a hole ("keyhole") of a complementary shape. Attachment of the first part to the second part is achieved by inserting the key through the keyhole and rotating along the axis of the elongated member. The amount of rotation may depend on the shape of the key and keyhole and/or additional structures or mechanisms within the cavity. After the attachment, the first part may not be separated from the second part without undergoing the reverse rotation, or rotating to some other position based on the shape of the key and keyhole. Preferably, the attached key and keyhole allow an electrical connection to be formed between the connection end of the conductor and the circuitry of the electronics module. In one embodiment, the electrical connection may not form until achieving a certain angle of rotation. Alternatively, the electrical connection may form regardless of the angle, so that inserting the elongated member into the cavity creates the electrical connection before rotating the electronics module. Thus, the conductor may be electrically connected to the electronics module without the electronics module being secured to the skull screw. In one embodiment, the shape on the elongated member is part of the insulated conduit. In another embodiment, the shape on the elongated member may be electrically-conductive and part of the electrode end of the conductor. The shape on the elongated member may be rectangular, triangular, cylindrical, or some other regular or irregular shape. The shape may be rotationally symmetric, as shown in FIG. 7A and the cross-section views of FIGS. 13A, 13B, 14, 15, 16A, 16B, and 17, or may be rotationally asymmetric, as shown in FIG. 12A.

Figure 12A:
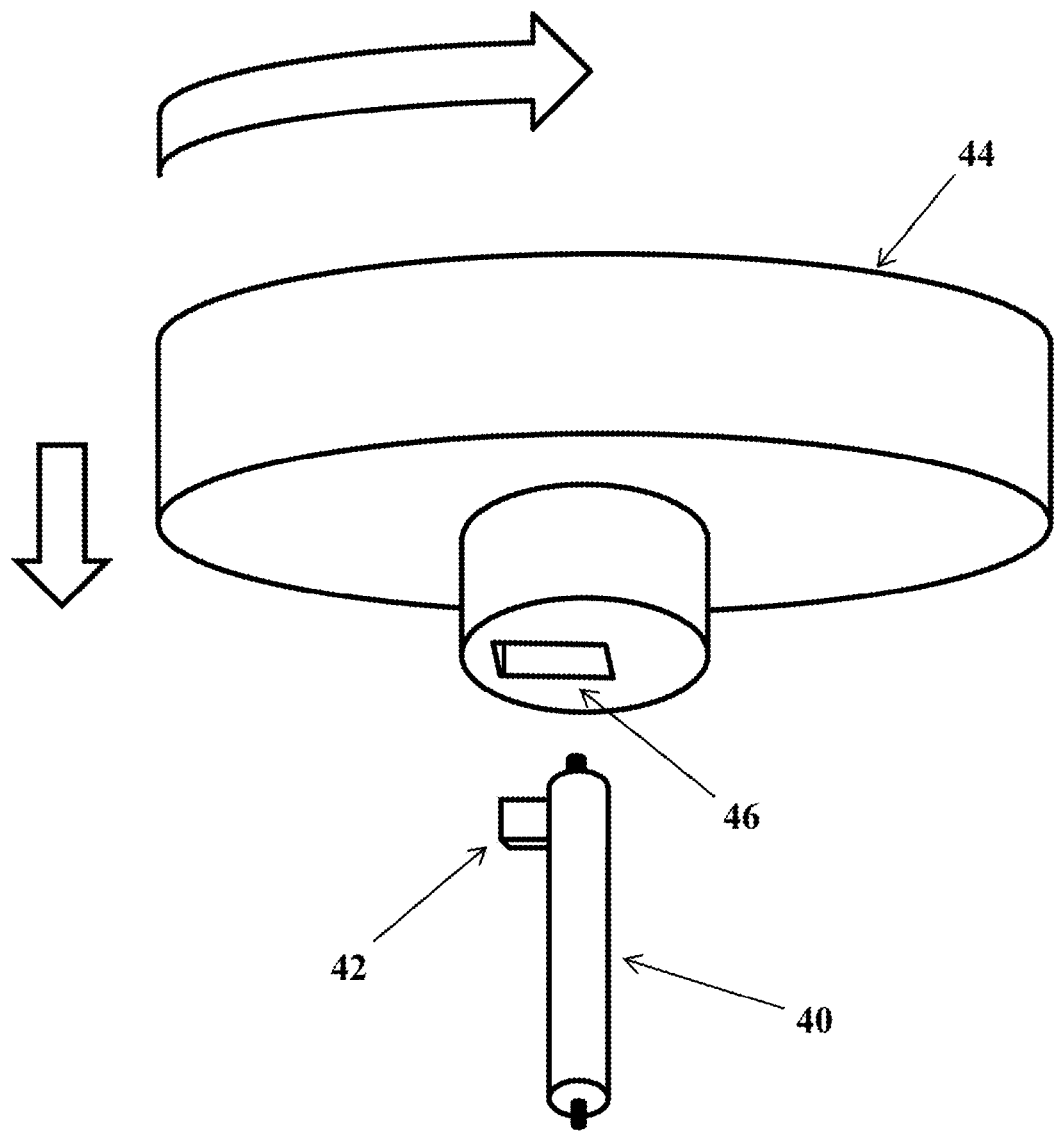
FIG. 12A shows an example key and keyhole attachment between an insulated conduit as a key and an electrode assembly as a keyhole.
Figure 12B:
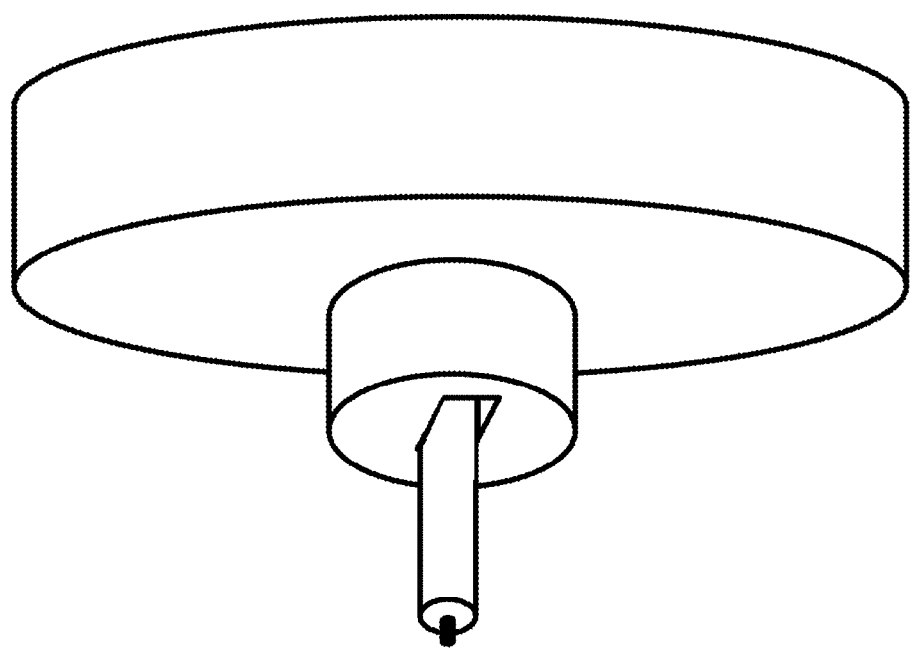
FIG. 12B shows the parts of FIG. 12A in a removably attached state.

For example, FIG. 12A shows a conductor housed in an insulated conduit 40 comprising a key with a rectangular shape 42 with an electronics module 44 comprising a complementary keyhole 46. For simplicity, the skull screw attached to the insulated conduit is not shown. The electronics module is pushed onto the insulated conduit, as shown by the straight block arrow, and rotated 90° counter-clockwise, as shown by the curved block arrow. The attached position is shown in FIG. 12B, wherein the connection end of the conductor forms an electrical connection with the circuitry of the electronics module. Separating the conductor and electronics module would require rotating 90° clockwise, though in one embodiment, a 270° counter-clockwise rotation may suffice. In one embodiment, a spring-loaded mechanism locks the electronics module at a certain angle to prevent unwanted rotation and separation. Similar to a bayonet mount, the electronics module may need to be pushed in towards the conductor in order to rotate and separate the two.

Figure 13A:
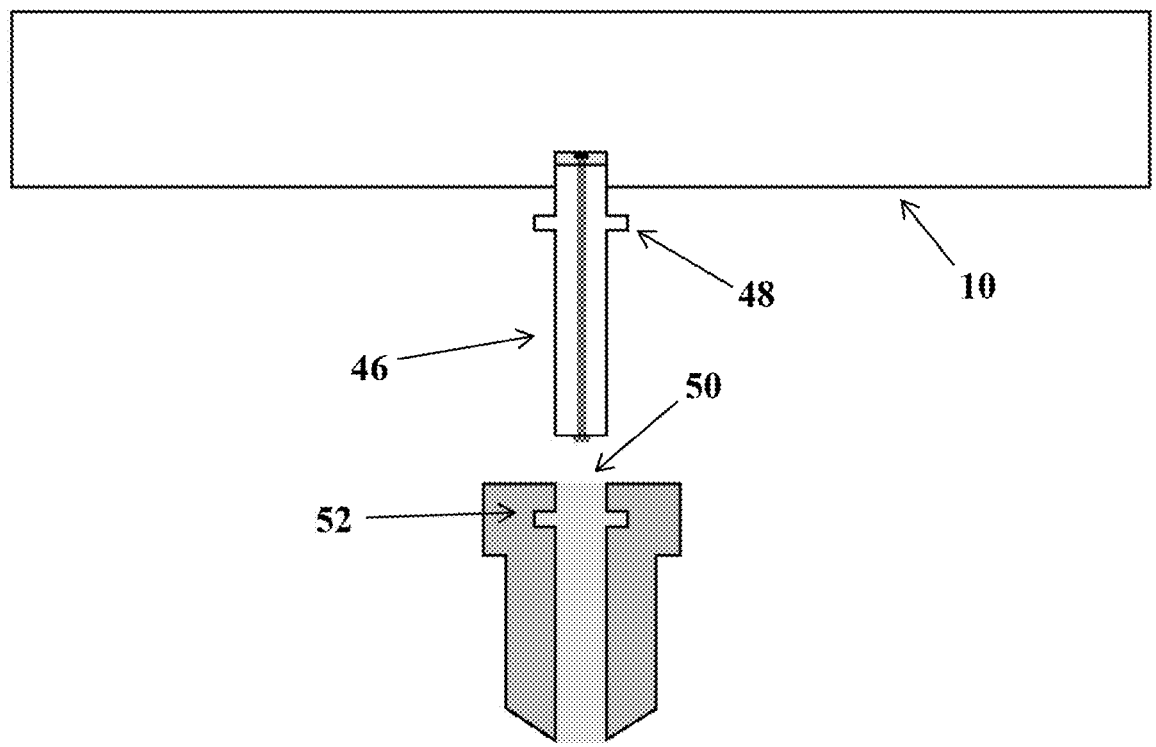
FIG. 13A shows a cross-section view of an implantable electrode assembly where the insulated conduit functions as a key and the head end of the skull screw functions as a keyhole in order to removably attach the two.

In one embodiment, the insulated conduit is removably attached to the head end of the skull screw by a key and keyhole mechanism, wherein the insulated conduit comprises a key and the head end of the skull screw comprises a complementary keyhole. FIG. 13A shows an example cross-section of an insulated conduit 46 with a rectangular shape 48. While attached to the electronics module 10, the insulated conduit is inserted into the head end 50 of the skull screw and the electronics module is turned to engage the shape in the cavity 52.

Figure 13B:
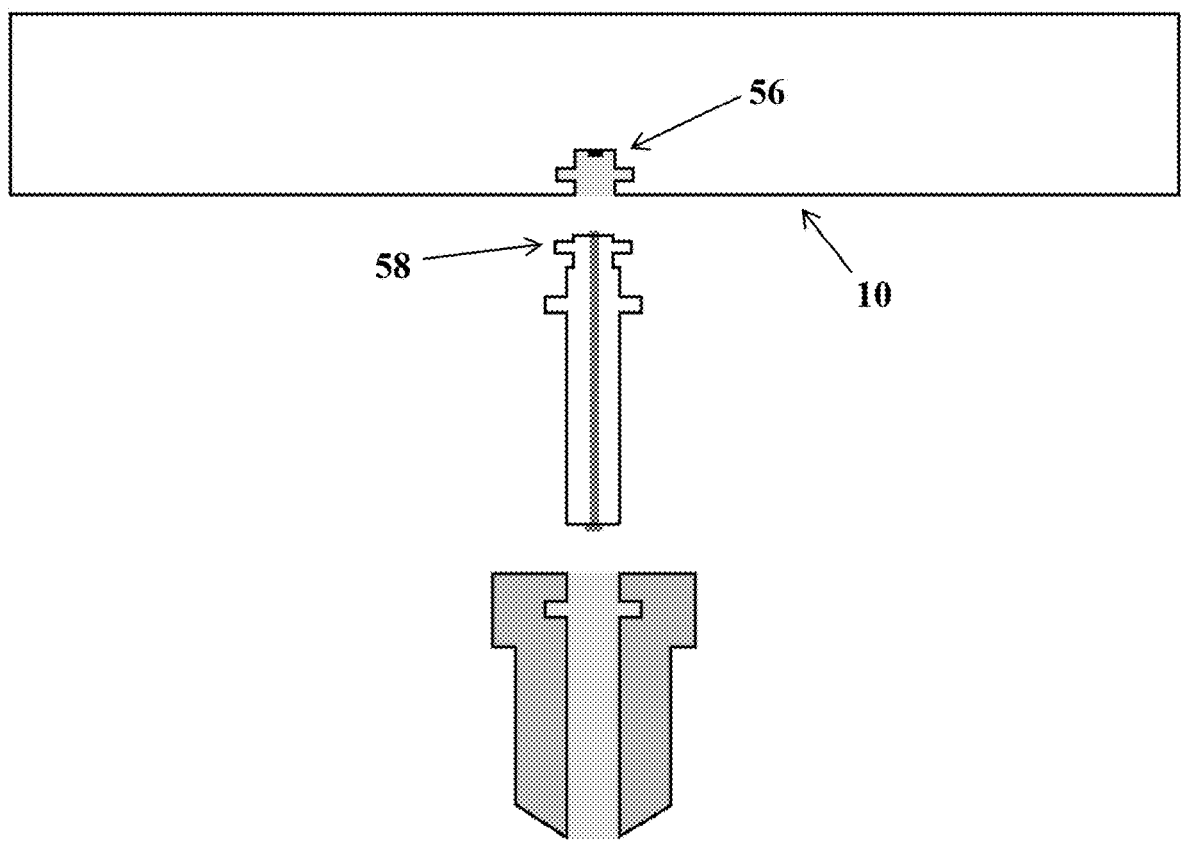
FIG. 13B shows an additional modification to FIG. 13A, where the connection end of the conductor functions as a key and the electronics module functions as a keyhole in order to removably attach the two.

In a further embodiment, the insulated conduit comprises a triangular key and the head end of the skull screw comprises a complementary triangular keyhole. FIG. 7A shows an equilateral triangular hole 24 centered on the skull screw head end and a complementary triangular shape 26 centered on the insulated conduit 12. The electronics module may be removably attached by inserting the insulated conduit into the skull screw so that the triangular form passes through the triangular hole, and by rotating the electronics module by 45-75°, preferably 50-70°, more preferably 55-65°, clockwise or counterclockwise, relative to the skull screw. Preferably, the insulated conduit remains attached to the electronics module when detaching the electronics module from the head end of the skull screw. In one embodiment, the connection end of the conductor may also be removably attached to the electronics module by a key and keyhole mechanism, for example, FIG. 13B shows a second key and keyhole mechanism between the two. The electronics module 10 comprises the cavity and keyhole 56 through which the connection end of the conductor 58 may be inserted and turned. In an alternative embodiment, the connection end of the conductor may be removably attached to the electronics module by a different mechanism.

Figure 15:
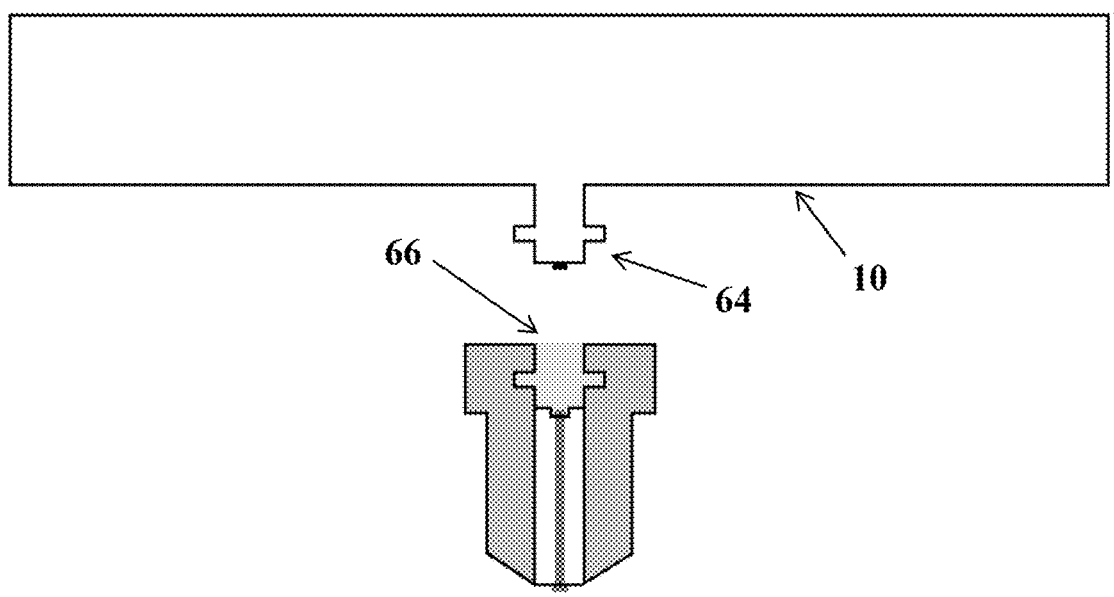
FIG. 15 shows a cross-section view of an implantable electrode assembly where the electronics module functions as a key and the head end of the skull screw functions as a keyhole in order to removably attach the two.

In one embodiment of the implantable electrode assembly, the head end of the skull screw is removably attached to the electronics module by a key and keyhole mechanism. In a further embodiment, the head end of the skull screw comprises a key and the electronics module comprises a complementary keyhole. FIG. 14 shows a cross-section view of an example mechanism where the electronics module 10 further comprises a keyhole and cavity 60 by which to receive the head end 62 of the skull screw. In a related embodiment, the electronics module comprises a projection that functions as a key and the head end of the skull screw comprises a complementary keyhole. FIG. 15 shows a cross-section view of an example of this embodiment where the electronics module 10 has the projection 64 that can fit within the cavity and keyhole 66 at the head end of the skull screw.

Figure 16A:
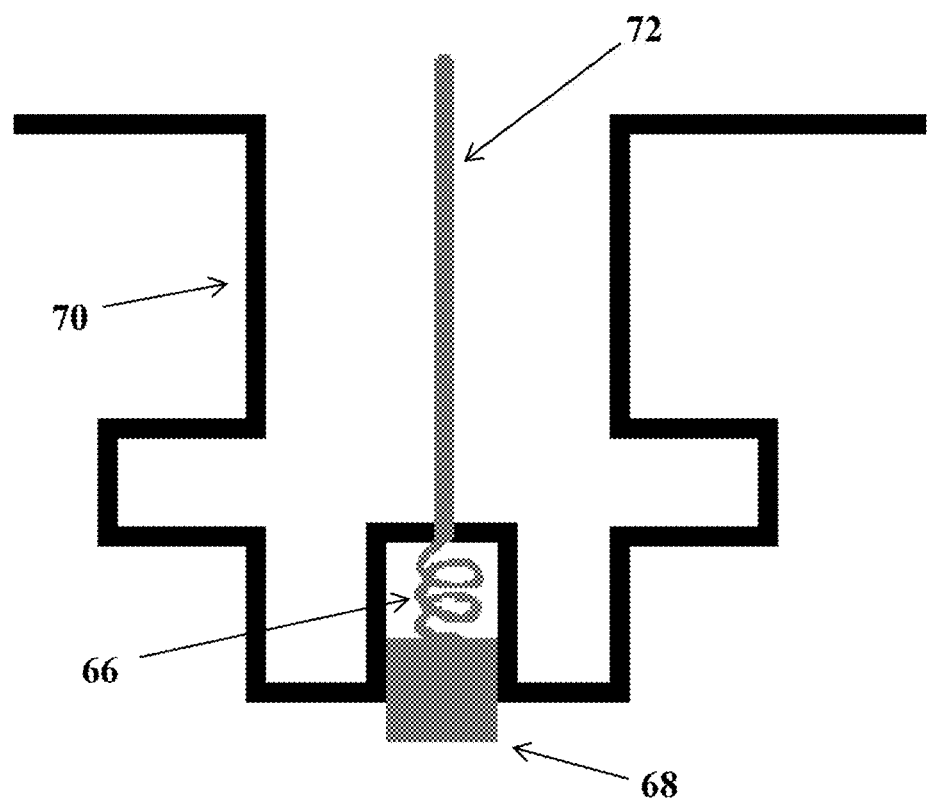
FIG. 16A shows an example arrangement of an electrically-conductive spring-loaded piston.
Figure 16B:
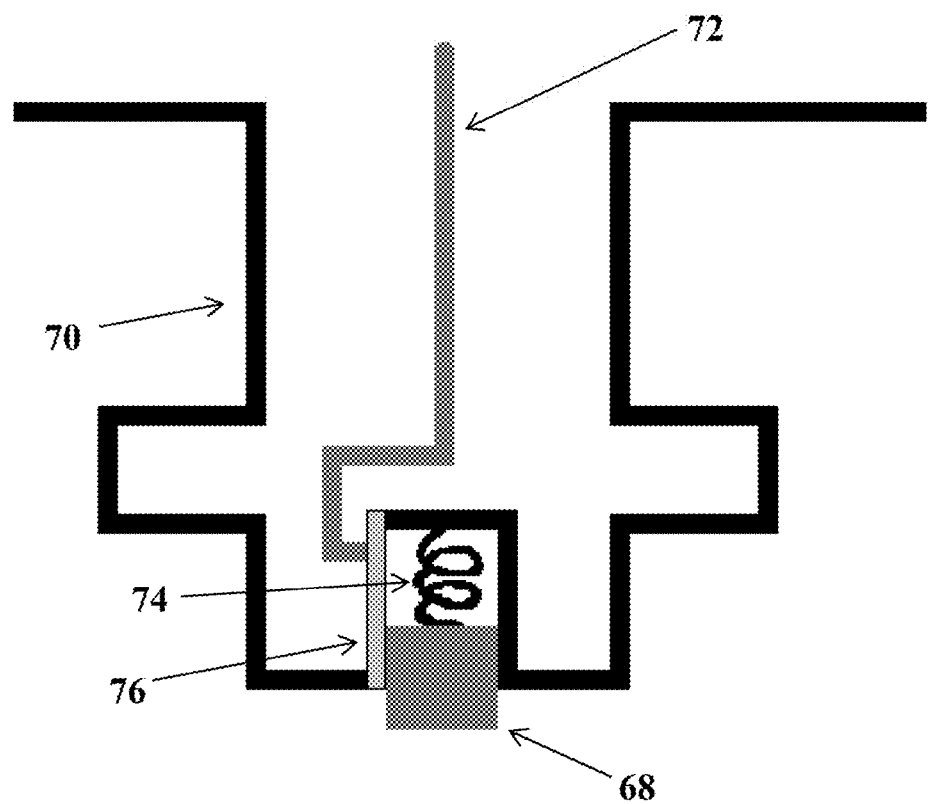
FIG. 16B shows another example arrangement of an electrically-conductive spring-loaded piston.

In a further embodiment, where the electronics module comprises a projection that functions as a key and the head end of the skull screw comprises a complementary keyhole, the end of the projection has an electrically-conductive spring-loaded piston. The projection and the electrically-conductive spring-loaded piston are configured to fit into a cavity in the head end of the skull screw and form both a locked position with the skull screw and an electrical connection with the connection end of the conductor. As discussed previously, a locked position may prevent unwanted rotation and separation of the removably attached parts of the implantable electrode assembly. The spring-loaded piston keeps the parts locked but allows for the two parts to be pushed together and rotated by hand. In one embodiment, the spring-loaded piston is electrically conductive in order to keep the connection end of the conductor electrically connected to the electronics module in the locked position. FIG. 15 shows an example key and keyhole configuration of this embodiment, with FIGS. 16A and 16B showing two examples of electrically-conductive spring-loaded pistons, though other configurations may be possible. In FIG. 16A, the spring 66 may comprise an electrically-conductive material in order to electrically connect the piston 68 at the end of the projection 70 with the wire 72 to the electronics of the electronics module. In FIG. 16B, the projection 70 similarly houses the wire 72 and electrically-conductive piston 68. However, the spring 74 does not form the electrical connection between the wire and the piston, instead, a side of the piston shaft 76 comprises a conductive material and is electrically connected to both piston and wire. In an alternative embodiment, an electrically-conductive spring may be used without a piston. In the embodiment where the conductor comprises more than one wire for forming more than one electrical connection with a patient's brain tissue, the end of the projection may comprise more than one piston. Alternatively, the end of the projection and the cavity of the electronics module could comprise multiple pins and sockets, or concentric conductive rings, in order to form multiple electrical connections.

Figure 17:
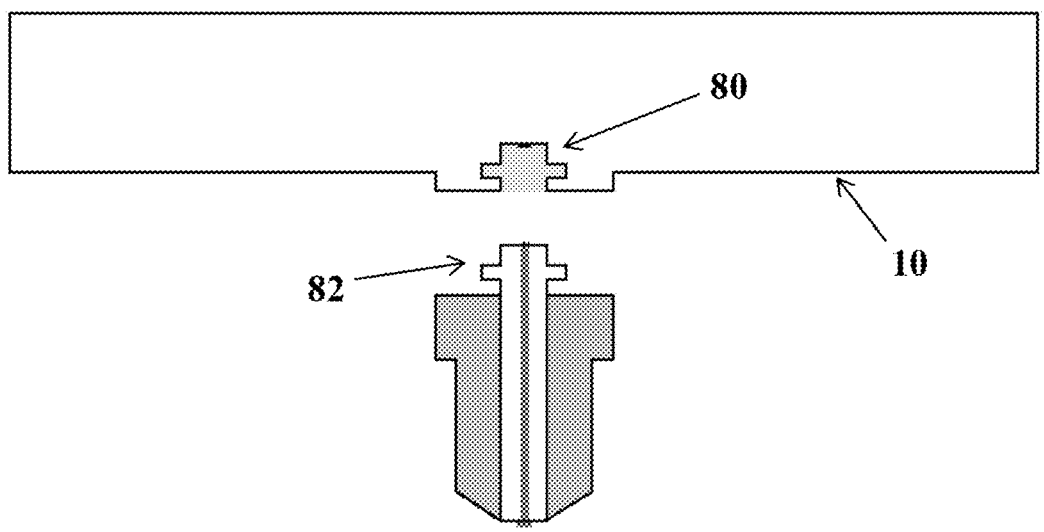
FIG. 17 shows a cross-section view of an implantable electrode assembly where the connection end of the conductor functions as a key and the electronics module functions as a keyhole in order to removably attach the two.

In one embodiment of the implantable electrode assembly, the insulated conduit is removably attached to the electronics module by a key and keyhole mechanism, wherein the insulated conduit comprises a key and the electronics module comprises a complementary keyhole. Preferably the insulated conduit remains attached within the skull screw. FIG. 17 shows a cross-section view of an example arrangement where the electronics module 10 comprises a keyhole and cavity 80 and the insulated conduit 82 near the connection end of the conductor comprises a key. This embodiment may be similar to the embodiment illustrated by FIG. 13B provided that the conductor and insulated conduit are kept within the skull screw while detaching the electronics module.

Figure 1:
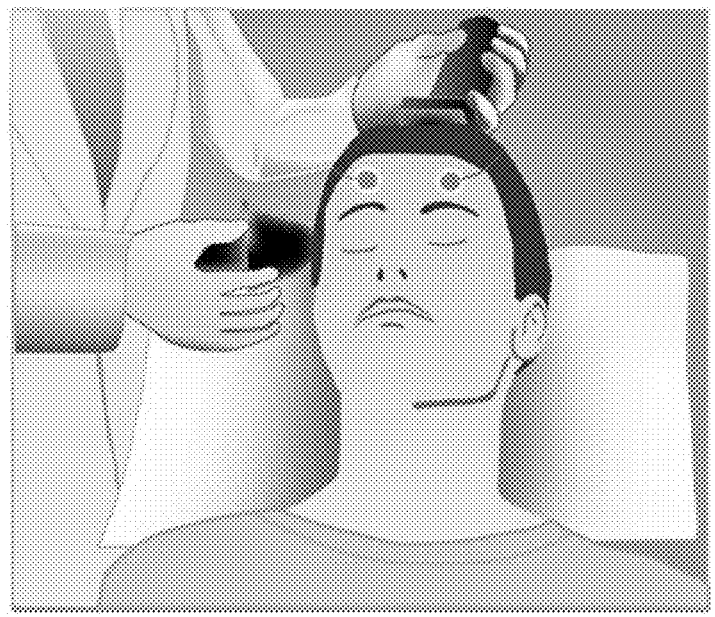
FIG. 1 is an illustration of a patient undergoing electroconvulsive therapy (ECT).
Figure 2:
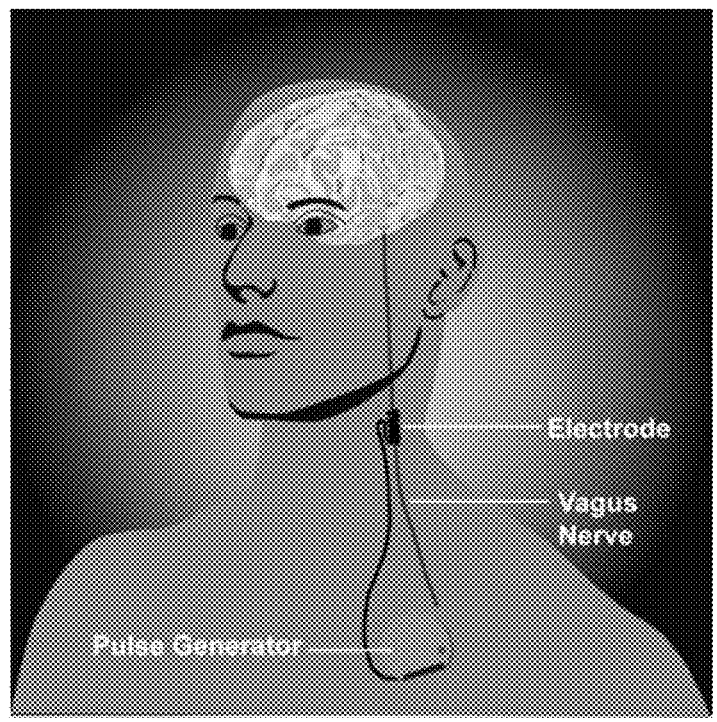
FIG. 2 is a diagram of a patient with an implanted vagus nerve stimulator (VNS).
Figure 3:
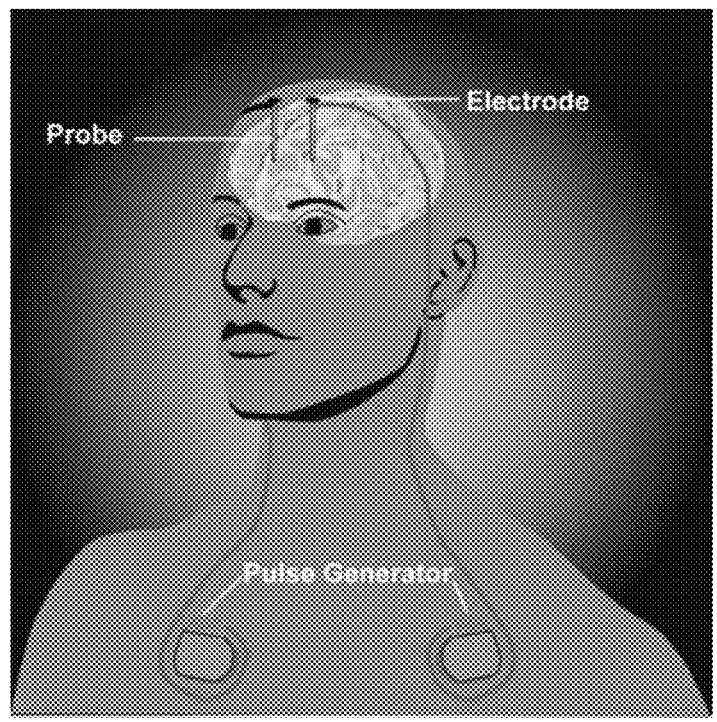
FIG. 3 is a diagram of a patient with an implanted deep brain stimulator (DBS).
Figure 4:
FIG. 4 is a photograph of an Ojemann Cortical Stimulator.
Figure 5:
FIG. 5 is photograph of brain tissue being stimulated by a dual electrode current from an Ojemann Cortical Stimulator.
Figure 6:
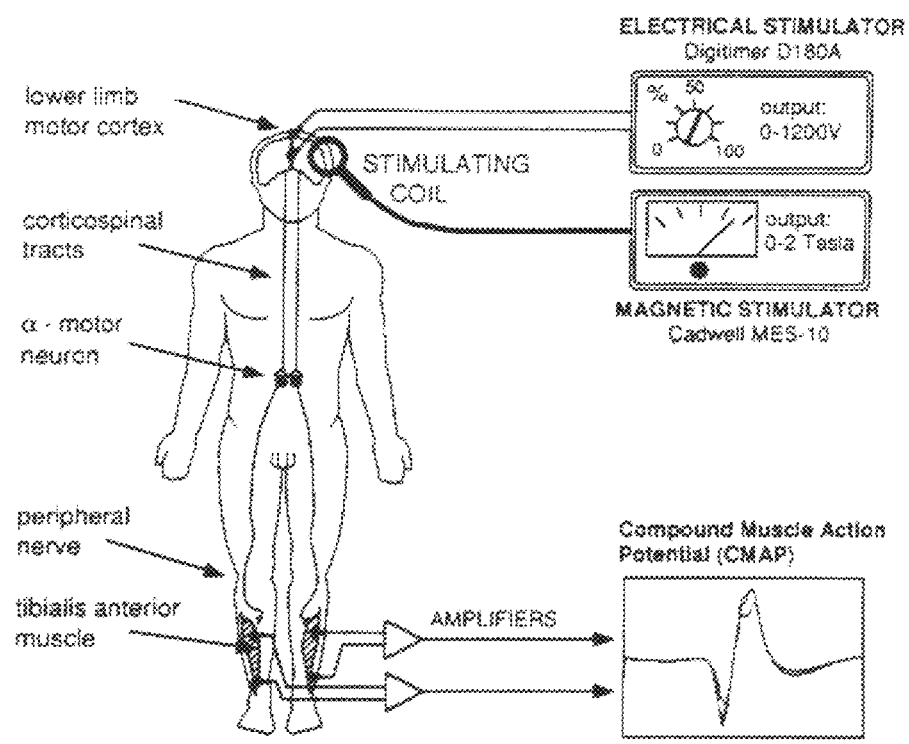
FIG. 6 is a diagram of a patient being stimulated by both magnetic fields and electric currents.

According to a second aspect, the present disclosure relates to a method of treating a medical ailment of a patient with the implantable electrode assembly that has a pulse generator. The method involves implanting the implantable electrode assembly into a skull of the patient. This implanting step may require surgery under anesthesia, and may involve shaving a portion of the patient's head and cutting a segment of the scalp to expose an exterior portion of the skull. A hole or incision in the patient's skull may be required by drilling or cutting the bone. Depending on the design of the electrode end and the insulated conduit, the insulated conduit may first be threaded through a hole in the patient's skull and placed at certain locations of the patient's brain tissue to form electrical connections. The electrode end may comprise wires placed for deep brain stimulation, as in FIG. 3, or more preferably, cortical stimulation on the surface of the brain tissue, as in FIG. 11. In one embodiment, where the electrode end of the conductor forms only a single electrical connection not far from the tip end of the skull screw, as in FIG. 7B, the skull screw may be inserted first, followed by the conductor housed in the insulated conduit. Alternatively, the skull screw may be inserted while the conductor and insulated conduit are kept in place in the skull screw. In that instance, the entire implantable electrode assembly may be inserted as one piece into a patient's skull. The electronics module may be attached to the skull screw during the implant surgery, or may be attached later, for instance, after a period of healing. In one embodiment, the electronics module may be located beneath the scalp while attached to the skull screw.

Preferably, the skull screw is inserted substantially perpendicularly to the skull surface, which means that the smallest angle formed between the rotational axis of the screw and the nearest skull surface is 70-90°, preferably 75-90°, more preferably 80-90°. In a preferred embodiment the skull screw is not implanted to a depth that would perturb or harm the patient's brain tissue, but is deep enough to form an electrical connection between the tip end and the patient's brain tissue. In a related embodiment, the diameter of the skull screw unthreaded head section and length of the shaft section are chosen so that the skull screw point end cannot penetrate far into the cranial cavity. For example, the length of the skull screw shaft section may be at most 9 mm, preferably at most 8 mm, more preferably at most 7 mm, and the unthreaded head section may have a diameter at least 1 mm, preferably at least 2 mm greater than the core diameter of the skull screw.

In an alternative embodiment, a receptacle for the screw is implanted into a patient's head, and the implantable electrode assembly is inserted into the receptacle. In another alternative embodiment, a hole is drilled into a patient's skull and an unthreaded skull screw is inserted and secured by osseointegration with the bone tissue. In another alternative embodiment, where the conductor and insulated conduit are inserted after implanting the skull screw, the hollow core of the skull screw may be used as a screw drive.

Following the successful implantation of the electrode assembly, the pulse generator may drive pulses of current between the electrode end of the conductor and the skull screw. The pulses may have widths of 10 µs-300 ms, preferably 50 µs-250 ms, more preferably 55 µs-200 ms, frequencies of 10-200 Hz, preferably 15-180 Hz, more preferably 20-160 Hz, and voltages of 0.1-6 V, preferably 0.2-5 V, more preferably 0.4-4.5 V. In the embodiment where the electrode end of the conductor forms two or more electrical connections, the pulse generator may drive pulses of current with similar parameters between those two or more electrical connections. The pulse generator may furthermore direct electricity to electrical connections on the brain through electrode arrangements that have been discussed previously. The pulse generator may also be able to monitor the amount of current delivered through the electrical connections. For instance, if the delivered current falls suddenly due to an increase in resistance or a break in the electrical connection, the pulse generator may be able to respond by suspending the electric stimulation.

The pulses of current on the brain tissue may send electrochemical waves on the cortex, subcortex, and associated neural axons. These electrochemical waves may activate or block neuronal activity, and may cause or inhibit the release of neurotransmitters at synapses. A neurologist may be able to determine the effective pulse parameters, electrode location, and length of treatment. A single session of neurostimulation may be administered for 20-60 minutes multiple times a day. These sessions may be at timed intervals, for example, every two hours. Alternatively, the sessions of neurostimulation may occur depending on a patient's brain activity, or may be manually turned on or off by the patient as needed. In one embodiment, the electrode assembly may deliver pulses of current continuously.

The medical ailment of the patient may be epilepsy, migraine, depression, anxiety, attention deficit disorder, hyperactivity, bipolar disorder, stroke, dementia, schizophrenia, delirium, neurosis, psychosis, Parkinson's disease, alcohol withdrawal, drug withdrawal, dizziness, motion sickness, insomnia, dystonia, chronic pain, obsessive compulsive disorder, Tourette's syndrome, essential tremor, spasticity, trigeminal neuralgia, and/or headache. Preferably the medical ailment is epilepsy, migraine, depression, anxiety, bipolar disorder, stroke, dementia, schizophrenia, delirium, neurosis, psychosis, Parkinson's disease, dystonia, chronic pain, obsessive compulsive disorder, Tourette's syndrome, essential tremor, spasticity, trigeminal neuralgia, and/or headache. More preferably the medical ailment is epilepsy, depression, anxiety, bipolar disorder, dementia, schizophrenia, delirium, neurosis, psychosis, Parkinson's disease, dystonia, chronic pain, obsessive compulsive disorder, Tourette's syndrome, essential tremor, spasticity, and/or trigeminal neuralgia. As used herein, to "treat" a medical ailment means to reduce or inhibit the progression, severity, and/or duration of the medical ailment or other accompanying symptoms. Another form of therapy may be combined with the electric stimulation, such as psychological counseling in the case of anxiety. It is possible for a patient to present more than one medical ailment and receive therapy for those medical ailments from a single implantable electrode assembly. For example, a patient may receive the electric stimulation as therapy for both anxiety and chronic pain.

In one embodiment of the method, the method also involves removing the electronics module while leaving the conductor and cannulated skull screw in place and attaching a second electronics module. Preferably, the electronics module may be removed by a physician in an outpatient clinic, and without the physician having to use specialized tools. The second electronics module may have a greater battery charge, different programs, more digital storage space, or some other difference. Alternatively, the first electronics module may be removed in order to charge the battery, transfer data, and/or transfer programs before returning the first electronics module to the conductor and cannulated skull screw on a patient's head. In one embodiment, the electronics module and the conductor may be removed from a patient's head while leaving the skull screw in place, and then reattaching the same electronics module and conductor or a different electronics module and/or conductor. In this embodiment, the removal and reattachment may be accomplished in a surgical environment as the patient's brain tissue may be exposed through the cannulated skull screw.

According to a third aspect, the present disclosure relates to a method of monitoring a patient's brain activity with the implantable electrode assembly. The implantable electrode assembly may be implanted as described previously, with the electrode end of the conductor forming at least two electrical connections with different locations in a person's brain. An implantable electrode assembly may be able to receive a patient's brain activity once an on/off switch of the electronics module is turned on. This brain activity may be digitized by the computer chip and stored in a digital storage medium as a recording of the brain activity. In the embodiment where the electronics module further comprises a wireless transceiver, the wireless transceiver may be able to transmit the recorded brain activity to a computer or wireless device for analysis by a physician. In one embodiment, the brain activity may be digitized and transmitted wirelessly without storing in the digital storage medium. As mentioned previously, the electronics module may further comprise surface electrodes attached to other places of a patient's scalp or other places of the body. The electronics module may then be able to record electric activity from these locations, for example, as an electrocardiogram. In one embodiment, a physician may be able to both monitor and adjust a patient's brain stimulation treatment remotely through the wireless transceiver.

In one embodiment, the electrode assembly may be able to deliver pulses of current based on received brain activity, for example, to increase or decrease a pulse parameter or parameters according to a certain characteristic of the brain activity. For example, if a patient's brain activity has been unchanged since receiving electric stimulation, the computer chip may respond by modifying the pulse width and/or frequency until a target brain activity is achieved. This feedback mechanism may also be used to avoid unwanted side-effects of brain stimulation. For instance, the electrode assembly may be able to detect a patient's brain activity that relates to sleep, and based on the assumption that the patient is sleeping, avoid certain pulse frequencies that may increase the patient's alertness. The electrode assembly may be able to use the same conductors for receiving brain activity and stimulating brain tissue, for instance, by switching between the two modes of receiving and stimulating. Or, some conductors may be used solely for receiving and some may be used solely for stimulation.

In another embodiment, the implantable electrode assembly may also assist patients with a sensory impairment. For instance, the electronics module of the implantable electrode assembly may comprise a microphone and a connection to an electrode array in a patient's cochlea. By electrically stimulating the cochlear nerve based on the microphone input, the electrode assembly may be able to function as a hearing aid.

The invention claimed is:

1. A method of treating a medical ailment of a patient with an implantable electrode assembly, the method comprising:
    implanting the implantable electrode assembly into a skull of the patient, wherein the implantable electrode assembly comprises:
        an electrically-conductive cannulated skull screw with a head end and a point end, which transverses the skull of the patient with the point end located at an interior surface of the skull and the head end located at an exterior surface of the skull,
        an electronics module comprising a casing, wherein the electronics module is electrically connected to the head end of the skull screw and wherein the casing is in direct contact with the head end of the skull screw,
        a conductor housed in an insulated conduit and threaded through the skull screw, said conductor comprising a connection end and an electrode end, with the connection end located at the head end of the skull screw and electrically connected to the electronics module,
a flexible insulator housing three conductive discs having diameters of 0.2-3 mm arranged linearly with an equal spacing of 4-12 mm for a total length of 3.5-9 cm, wherein each conductive disc is wired independently and electrically connected to the electrode end;
forming three electrical connections with the conductive discs and different locations of the patient's brain tissue; and
continuously generating pulses of current between the conductive discs and the skull screw to inhibit the release of neurotransmitters, wherein the pulses have square pulse shapes with pulse widths of 55 µs-200 ms, frequencies of 20-160 Hz, and voltages of 0.4-4.5 V,
wherein the medical ailment is at least one selected from the group consisting of epilepsy, migraine, depression, anxiety, attention deficit disorder, hyperactivity, bipolar disorder, stroke, dementia, schizophrenia, delirium, neurosis, psychosis, Parkinson's disease, alcohol withdrawal, drug withdrawal, dizziness, motion sickness, insomnia, dystonia, chronic pain, obsessive compulsive disorder, Tourette's syndrome, essential tremor, spasticity, trigeminal neuralgia, and headache.

2. The method of claim 1, further comprising:
generating additional pulses of current between two of the three conductive discs with pulse widths of 55 µs-200 ms, frequencies of 20-160 Hz, and voltages of 0.4-4.5 V, wherein the additional pulses are sine waves.

3. The method of claim 2, wherein the medical ailment is motion sickness.

4. The method of claim 3, further comprising drilling a hole into the patient's skull before the implanting.

5. The method of claim 3, further comprising monitoring the amount of current delivered by the pulses of current and the additional pulses of current.

6. The method of claim 3, further comprising stimulating the brain tissue with pulses of magnetic fields, wherein the electrode end of the conductor comprises an electromagnet.

7. The method of claim 2, wherein the medical ailment is both anxiety and chronic pain.

8. The method of claim 7, wherein the generating additional pulses of current between the two of the three conductive discs is done for 20-60 minutes every two hours.

9. The method of claim 7, further comprising drilling a hole into the patient's skull before the implanting.

10. The method of claim 7, further comprising stimulating the brain tissue with pulses of magnetic fields, wherein the electrode end of the conductor comprises an electromagnet.

11. The method of claim 2, further comprising implanting a receptacle for the skull screw into the patient's skull before the implanting the implantable electrode assembly.

12. The method of claim 2, wherein the generating additional pulses of current between the two of the three conductive discs is done continuously.

13. The method of claim 12, wherein the medical ailment is dementia.

14. The method of claim 2, wherein the medical ailment is insomnia, and one conductive disc forms an electrical connection with a brain tissue of Broadman Area 4.

15. The method of claim 1, further comprising:
removing the electronics module while leaving the conductor and cannulated skull screw in place; and
attaching a second electronics module.

16. The method of claim 15, wherein the electronics module is removed without having to use specialized tools.

17. The method of claim 16, wherein the insulated conduit is removably attached to the head end of the skull screw by a key and keyhole mechanism, wherein the insulated conduit comprises a key and the head end of the skull screw comprises a complementary keyhole.

18. The method of claim 15, wherein the electronics module and the second electronics module each further comprises a battery, and the second electronics module has a greater battery charge.

* * * * *